(12) United States Patent
Li et al.

(10) Patent No.: US 11,751,838 B2
(45) Date of Patent: Sep. 12, 2023

(54) SYSTEMS AND METHODS FOR CONTROLLING AN X-RAY TUBE FILAMENT

(71) Applicant: SHANGHAI UNITED IMAGING HEALTHCARE CO., LTD., Shanghai (CN)

(72) Inventors: Hua Li, Shanghai (CN); Jiawen Zhou, Shanghai (CN); Yifeng Jiang, Shanghai (CN); Tao He, Shanghai (CN); Yong Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 193 days.

(21) Appl. No.: 17/134,552

(22) Filed: Dec. 28, 2020

(65) Prior Publication Data

US 2021/0113177 A1    Apr. 22, 2021

Related U.S. Application Data

(63) Continuation of application No. 15/798,568, filed on Oct. 31, 2017, now Pat. No. 10,874,372, which is a (Continued)

(30) Foreign Application Priority Data

Feb. 22, 2016   (CN) .......................... 201610096480.5

(51) Int. Cl.
*A61B 6/03*       (2006.01)
*H05G 1/34*       (2006.01)
(Continued)

(52) U.S. Cl.
CPC .............. *A61B 6/582* (2013.01); *A61B 6/032* (2013.01); *H05G 1/265* (2013.01); *H05G 1/34* (2013.01)

(58) Field of Classification Search
None
See application file for complete search history.

(56) References Cited

U.S. PATENT DOCUMENTS 4,366,575 A   12/1982   Bax
4,775,992 A   10/1988   Resnick et al.
(Continued)

FOREIGN PATENT DOCUMENTS

CA    1193751 A     9/1985
CN    201854495 U   6/2011
(Continued)

OTHER PUBLICATIONS

Search report in International Application No. PCT/CN2017/074306 dated May 25, 2017, 8 pages.
(Continued)

*Primary Examiner* — Thomas R Artman
(74) *Attorney, Agent, or Firm* — METIS IP LLC

(57) ABSTRACT

This application discloses a method for calibrating filament current data of an X-ray tube. The method includes obtaining a first value of tube current to be calibrated and a value of filament current to be calibrated, the tube current to be calibrated and the filament current to be calibrated corresponding to a first calibration point; performing an emission operation based on the first value of the tube current to be calibrated and the value of the filament current to be calibrated; determining an actual value of the tube current during the emission operation; determining a difference between the actual value of the tube current and the first
(Continued)

value of the tube current to be calibrated; and calibrating, based on the difference, the first calibration point.

19 Claims, 12 Drawing Sheets

Related U.S. Application Data continuation of application No. PCT/CN2017/074306, filed on Feb. 21, 2017.

(51) Int. Cl.
*A61B 6/00* (2006.01)
*H05G 1/26* (2006.01)

(56) References Cited

U.S. PATENT DOCUMENTS

| | | | |
|---|---|---|---|
| 5,077,773 A | 12/1991 | Sammon | |
| 7,023,960 B2 | 4/2006 | Chretien | |
| 7,079,622 B2* | 7/2006 | Chretien | H05G 1/34 378/109 |
| 9,232,620 B2* | 1/2016 | Tajima | A61B 6/542 |
| 10,874,372 B2* | 12/2020 | Li | A61B 6/582 |
| 2004/0264643 A1* | 12/2004 | Chretien | H05G 1/34 378/109 |
| 2005/0084070 A1 | 4/2005 | Chretien | |
| 2008/0152073 A1 | 6/2008 | Fujimoto et al. | |
| 2013/0148784 A1* | 6/2013 | Tajima | A61B 6/4283 378/62 |
| 2016/0038114 A1 | 2/2016 | Tajima | |
| 2016/0088718 A1 | 3/2016 | Jiang | |
| 2017/0094763 A1 | 3/2017 | Liu et al. | |
| 2018/0064410 A1* | 3/2018 | Li | A61B 6/582 |
| 2021/0113177 A1* | 4/2021 | Li | A61B 6/032 |

FOREIGN PATENT DOCUMENTS

| | | | |
|---|---|---|---|
| CN | 104470175 A | | 3/2015 |
| CN | 105246240 A | | 1/2016 |
| CN | 105430858 A | | 3/2016 |
| JP | 2009081034 A | * | 4/2009 |
| JP | 2009081034 A | | 4/2009 |
| JP | 5939877 B2 | | 6/2016 |

OTHER PUBLICATIONS

First office action in Chinese Application No. 201610096480.5 dated Jul. 14, 2017, 13 pages.

* cited by examiner

SYSTEMS AND METHODS FOR CONTROLLING AN X-RAY TUBE FILAMENT

CROSS-REFERENCE TO RELATED APPLICATIONS

This application is a continuation of U.S. patent application Ser. No. 15/798,568, filed on Oct. 31, 2017, which is a continuation of International Application No. PCT/CN2017/074306, filed on Feb. 21, 2017, which claims priority of Chinese Application No. CN201610096480.5 filed on Feb. 22, 2016. The disclosures of the above-referenced applications are expressly incorporated herein by reference in their entirety.

TECHNICAL FIELD

This application relates to medical imaging, and more particularly, relates to systems and methods for controlling an X-ray tube filament of the medical imaging device.

BACKGROUND

A computed tomography (CT) device has a wide range of applications in the field of medical imaging. In a CT imaging process, an X-ray tube can be used for emission. Since the density of different tissues is different and the absorption degree of different tissues to X-ray is different, the CT device can complete the image of human tissues. In different CT scanning scenes, the operating parameters of a single X-ray tube filament (e.g., filament preheating current, preheating time) may cause the filament temperature to be too high or too low, and therefore cannot meet imaging requirements of different CT scans. Implementing calibration of the X-ray tube filament accurately and efficiently is still a difficulty at this stage. Therefore, systems and methods are needed to solve the above problem.

SUMMARY

This application discloses systems and methods for X-ray tube filament control.

According to one aspect of the present disclosure, a method for calibrating filament current data of an X-ray tube is provided. The method may include obtaining a first value of tube current to be calibrated and a value of filament current to be calibrated, the tube current to be calibrated and the filament current to be calibrated corresponding to a first calibration point; performing an emission operation based on the first value of the tube current to be calibrated and the value of the filament current to be calibrated; determining an actual value of the tube current during the emission operation; determining a difference between the actual value of the tube current and the first value of the tube current to be calibrated; and calibrating, based on the difference, the first calibration point.

According to another aspect of the present disclosure, a system for calibrating filament current data of an X-ray tube is provided. The system may include a calibration module and a preheating module. The calibration module may be configured to obtain a first value of tube current to be calibrated and a value of filament current to be calibrated, the tube current to be calibrated and the filament current to be calibrated corresponding to a first calibration point; perform an emission operation based on the first value of the tube current to be calibrated and the value of the filament current to be calibrated; determine an actual value of the tube current during the emission operation; determine a difference between the actual value of the tube current and the first value of the tube current to be calibrated; and calibrate, based on the difference, the first calibration point.

According to another aspect of the present disclosure, a non-transitory computer readable medium is provided, including executable instructions that, when executed by at least one processor, cause the at least one processor to effectuate a method. The method may include calibrating filament current data of an X-ray tube. The method may include obtaining a first value of tube current to be calibrated and a value of filament current to be calibrated, the tube current to be calibrated and the filament current to be calibrated corresponding to a first calibration point; performing an emission operation based on the first value of the tube current to be calibrated and the value of the filament current to be calibrated; determining an actual value of the tube current during the emission operation; determining a difference between the actual value of the tube current and the first value of the tube current to be calibrated; and calibrating, based on the difference, the first calibration point.

In some embodiments, calibrating, based on the difference, the first calibration point may include determining whether the difference is satisfied with a preset condition; and generating, if the difference is satisfied with the preset condition, filament current calibration data corresponding to the first calibration point.

In some embodiments, determining whether the difference is satisfied with the preset condition may include determining whether the difference is larger than a first threshold and smaller than a second threshold.

In some embodiments, calibrating, based on the difference, the first calibration point may further include if the difference is not satisfied with the preset condition, updating the first value of the tube current to be calibrated with the actual value of the tube current, and generating the filament current calibration data corresponding to the first calibration point based on the updated first value of tube current to be calibrated and the value of the filament current to be calibrated.

In some embodiments, generating the filament current calibration data corresponding to the first calibration point based on the updated first value of the tube current to be calibrated and the value of the filament current to be calibrated may further include, assigning an initial value to an iteration number; updating the iteration number based on a situation of updating the first value of the tube current to be calibrated to the actual value of the tube current; comparing the iteration number with an iteration-number threshold, and reporting an error if the iteration number is larger than the iteration-number threshold.

In some embodiments, the actual value of the tube current may correspond to at least one of a value of the tube current at an emission time point during the emission operation, or an average value of a plurality of values of the tube current at a plurality of emission time points during the emission operation.

In some embodiments, the method may further include calibrating a plurality of calibration points, the plurality of calibration points corresponding to a value of tube voltage, the plurality of calibration points including the first calibration point and a second calibration point, the second calibration point corresponding to at least a second value of the tube current to be calibrated, the first value of the tube current to be calibrated being in a first interval, the second tube current value to be calibrated being outside the first interval.

In some embodiments, the method may further include calibrating the first calibration point to determine fourth filament current calibration data; performing, based on the fourth filament current calibration data, data fitting; determining, based on a result of the data fitting, the second value of the tube current to be calibrated corresponding to the value of the tube voltage value; and determining, based on the second value of the tube current to be calibrated, the second calibration point.

In some embodiments, the method may further include determining first filament current calibration data corresponding to a first value of tube voltage; determining second filament current calibration data corresponding to a second value of the tube voltage; and determining third filament current calibration data corresponding to a third value of the tube voltage based on a difference between the first value of the tube voltage and the second value of the tube voltage, and at least one of the first filament current calibration data or the second filament current calibration data.

According to yet another aspect of the present disclosure, a method for preheating a filament of an X-ray tube is provided. The method may include determining a value of tube voltage, a value of tube current, a start time for emission, and a start time for preheating; determining, based on the start time for emission and the start time for preheating, a time length of preheating of the filament; establishing a heating model; determining a filament preheating plan according to the value of the tube voltage, the value of the tube current, the time length of preheating of the filament, and the heating model; and performing, based on the filament preheating plan, a filament preheating operation.

According to yet another aspect of the present disclosure, a system for preheating a filament of an X-ray tube is provided. The system may include a preheating module. The preheating module may be configured to determine a value of tube voltage, a value of tube current, a start time for emission, and a start time for preheating. The preheating module may be configured to determine, based on the start time for emission and the start time for preheating, a time length of preheating of the filament; establish a heating model; determine a filament preheating plan according to the value of the tube voltage, the value of the tube current, the time length of preheating of the filament and the heating model; and perform, based on the filament preheating plan, a filament-preheating operation.

According to yet another aspect of the present disclosure, a non-transitory computer readable medium is provided, including executable instructions that, when executed by at least one processor, cause the at least one processor to effectuate a method. The method may be used for preheating a filament of an X-ray tube. The method may include determining a value of tube voltage, a value of tube current, a start time for emission, and a start time for preheating; determining, based on the start time for emission and the start time for preheating, a time length of preheating of the filament; establishing a heating model; determining a filament preheating plan according to the value of the tube voltage, the value of the tube current, the time length of preheating of the filament and the heating model; and performing, based on the filament preheating plan, a filament-preheating operation.

In some embodiments, the method for preheating the filament of the X-ray tube may further include determining, based on the heating model, time information corresponding to a value of filament preheating current corresponding to the filament preheating plan, and the filament preheating plan may include the value of the filament preheating current and the time information corresponding to the value of the filament preheating current.

In some embodiments, the heating model may include a time length of a first standard preheating and a time length of a second standard preheating, and determining, based on the heating model, the time information corresponding to the value of the filament preheating current corresponding to the filament preheating plan may include comparing the time length of preheating of the filament with the time length of the first standard preheating and the time length of the second standard preheating; if the time length of preheating of the filament is smaller than the time length of the first standard preheating, determining the value of the filament preheating current as a first filament preheating current; if the time length of preheating of the filament is larger than or equal to the time length of the first standard preheating and smaller than the time length of the second standard preheating, determining the value of the filament preheating current as a second filament preheating current; and if the time length of preheating of the filament is larger than or equal to the time length of the second standard preheating, determining the value of the filament preheating current as a third filament preheating current.

In some embodiments, performing, based on the filament preheating plan, the filament-preheating operation may include determining whether an instruction of an X-ray loading plan is received, and performing, based on the determination as to whether an instruction of an X-ray loading plan is received, at least one operation.

In some embodiments, performing, based on the determination as to whether an instruction of an X-ray loading plan is received, the at least one operation may include determining, based on a determination of not receiving the instruction of an X-ray loading plan, a time length beyond the time length of preheating; and updating, based on the time length beyond the time length of preheating, the filament preheating plan.

In some embodiments, performing, based on the determination as to whether an instruction of an X-ray loading plan is received, the at least one operation may include performing, based on a determination of receiving the instruction of an X-ray loading plan, the instruction of the X-ray loading plan.

In some embodiments, determining the filament preheating plan may further include determining an initial value or an equivalent description value of a filament temperature, and determining, based on the initial value or the equivalent description value of the filament temperature, the filament preheating plan.

In some embodiments, determining the initial value or the equivalent description value of the filament temperature may further include obtaining a first emission plan and a second emission plan; determining, based on the first emission plan and the second emission plan, the initial value or the equivalent description value of the filament temperature.

In some embodiments, determining, based on the initial value or the equivalent description value of the filament temperature, the filament preheating plan may further include determining an emission time interval between an end time for emission of the first emission plan and a start time for emission of the second emission plan; determining a difference between a value of the tube current of the first emission plan and a value of the tube current of the second emission plan; determining a time length of preheating of a second emission based on the difference and a heating model; comparing the emission time interval with the time length of preheating of the second emission; and reporting an error when the emission time interval is smaller than the time length of preheating of the second emission.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

FIG. 11 illustrates a flowchart of an exemplary process for filament preheating plan generation according to some embodiments of the present disclosure; and.

DETAILED DESCRIPTION

Figure 1:
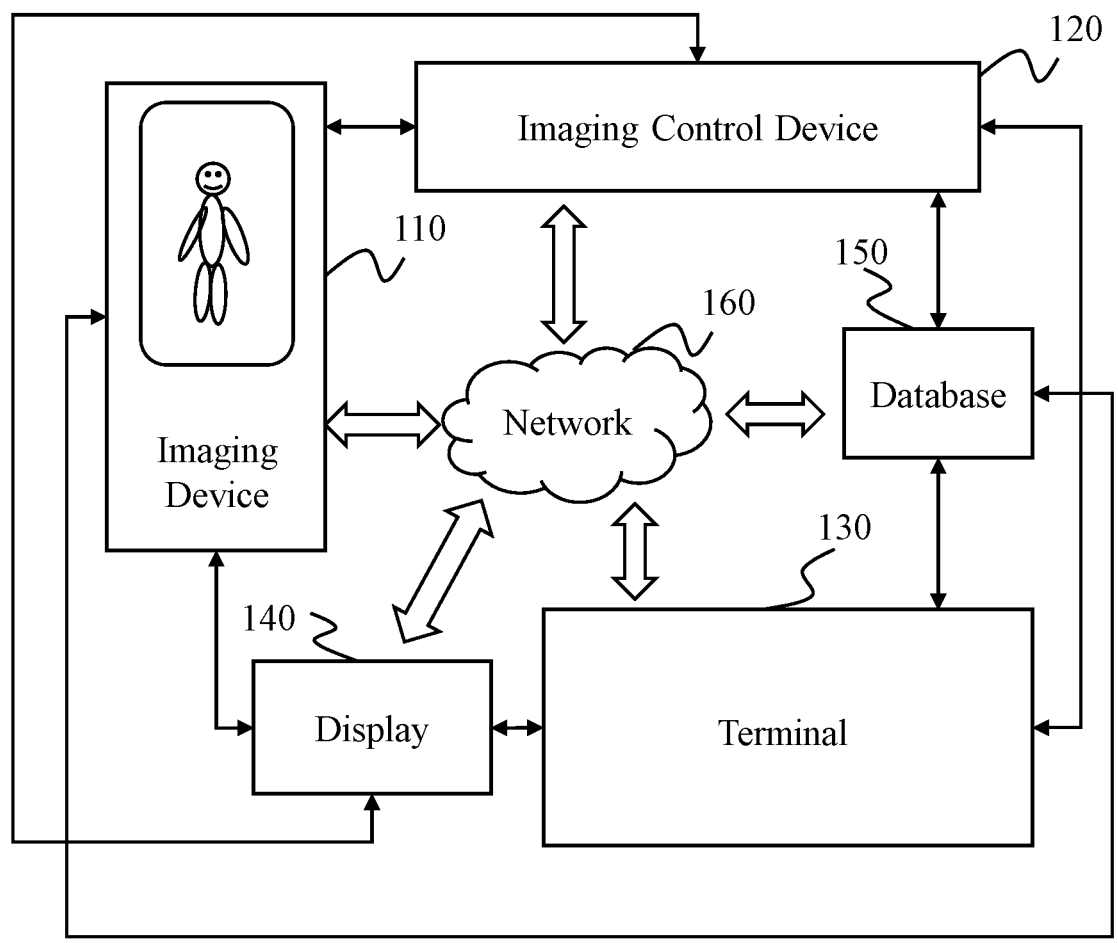
FIG. 1 illustrates an application scene schematic diagram of an exemplary imaging system according to some embodiments of the present disclosure.

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure or operation.

As used in the disclosure and the appended claims, the singular forms "a," "an," and "the" include plural referents unless the content clearly dictates otherwise. In general, the terms "comprises," "comprising," "includes," and/or "including" when used in the disclosure, specify the presence of stated steps and elements, but do not preclude the presence or addition of one or more other steps or elements.

Some modules of the data processing system may be referred to in various ways according to some embodiments of the present disclosure. However, any number of different modules may be used and operated in a client terminal and/or a server connected to the system via a network. These modules are intended to be illustrative, and different modules may be used in different aspects of the system and method.

According to some embodiments of the present disclosure, flowcharts are used to illustrate the operations performed by the system. It is to be expressly understood that the operations above or below may or may not be implemented in order. Conversely, the operations may be performed in inverted order, or simultaneously. Besides, one or more other operations may be added to the flowcharts, or one or more operations may be omitted from the flowcharts.

This application relates to medical imaging, and more particularly, relates to a system and method for X-ray tube filament control of the medical imaging system. The method for X-ray tube filament control may include calibrating filament current and generating a filament preheating plan.

The filament control system may calibrate the corresponding relationship between the filament current and tube current for a point to be calibrated during the calibration of the filament current. The point to be calibrated may be a data point consisting of a value of filament current and a value of tube current and corresponding to a certain size of a focal point and tube voltage. In the calibration process, for a value of the tube current to be calibrated, the filament control system may perform an emission operation and obtain an actual value of the tube current in the emission process. The filament control system may compare the value of the tube current to be calibrated and the actual value of the tube current, and calculate the difference between these two values. The filament control system may calibrate the value of the tube current to be calibrated based on the difference. For example, if the difference is satisfied with a certain preset condition, the filament control system may record the actual value of the tube current and the value of the filament current as a set of calibrated filament current calibration data. As another example, if the difference is not satisfied the preset condition, the filament control system may update the value of the tube current to be calibrated to the actual value of the tube current, and perform the above calibration process again until a certain number of iterations are completed or the filament current calibration data satisfied the above conditions are obtained.

The filament control system may obtain filament current calibration data of a calibration point where the value of the tube current is within a certain range based on the above method for the same focal point and the same value of the tube voltage. The filament control system may fit the filament current calibration data and obtain fitting values of a set of calibration points where the value of the tube current is outside the above range. Based on these fitting values, the filament control system may perform the calibration of the method above to generate new filament current calibration data. In some embodiments, if these fitting values are too large or too small endpoint data, the filament control system may directly apply the fitting values as filament current calibration data in order to avoid filament overcurrent and the like. Based on the above method, the filament control system may obtain a set of filament current calibration data corresponding to the value of the tube voltage.

For different values of the tube voltage, the filament control system may generate different filament current calibration data based on the above method. For example, the filament control system may generate the first filament current calibration data corresponding to a first value of the tube voltage and may generate the second filament current calibration data corresponding to a second value of the tube voltage. The filament control system may generate third filament current calibration data corresponding to a third value of the tube voltage using the interpolation algorithm based on the first filament current calibration data and the second filament current calibration data.

The filament preheating plan may include one or more filament preheating currents and time information (e.g., one or more time points, time periods) corresponding to the one or more filament preheating currents. A method of the filament control system may be applied to different scenes during the generation of the filament current preheating plan. In one scene, the filament control system may determine a filament preheat plan based on the emission start time in an emission plan and a value of an emission tube current. In one scene, the time interval between the previous emission and the next emission is relatively short, and the X-ray tube filament is not completely cooled. The filament control system may generate a filament preheating plan based on the previous emission plan and the current emission plan. In one scene, an imaging system fails to receive an X-ray emission instruction after the preheating plan is performed. The filament control system may update the preheating plan based on the X-ray emission instruction to prevent overheating.

Figure 2:
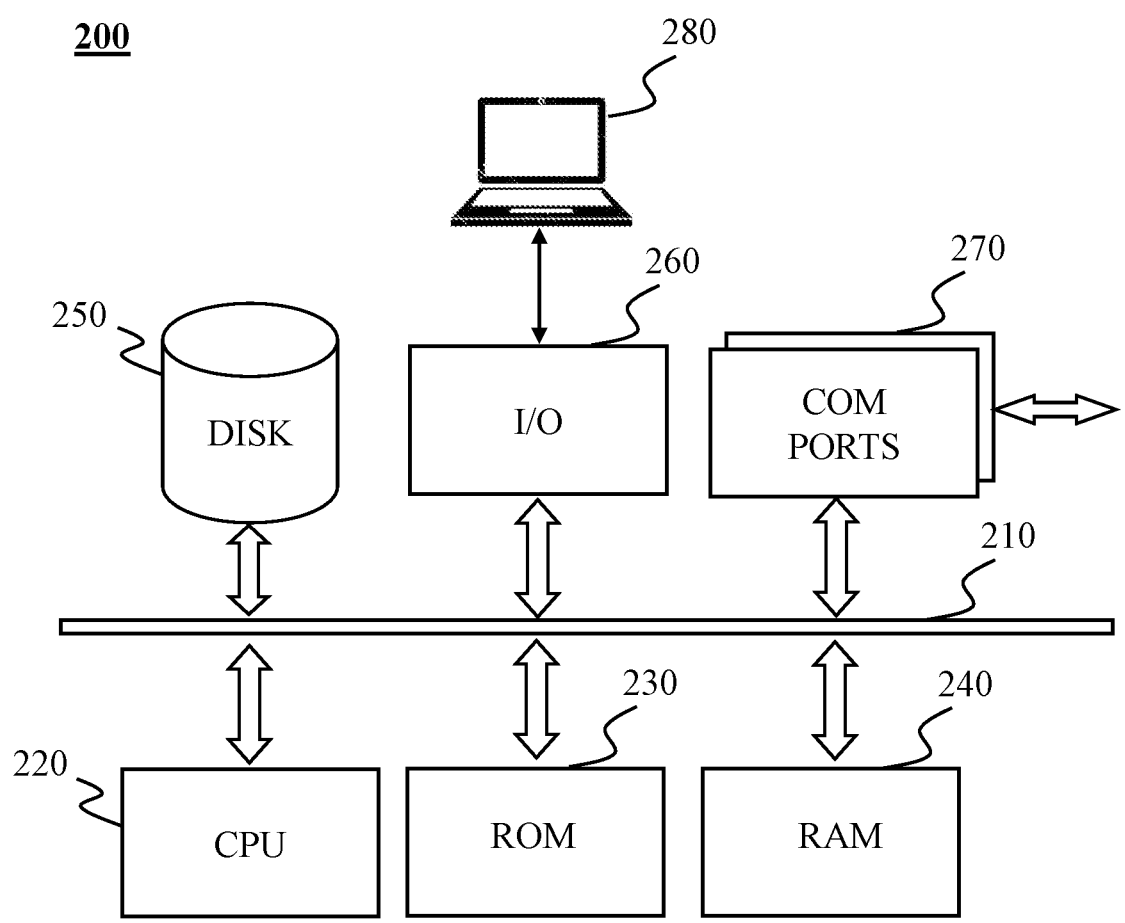
FIG. 2 illustrates a schematic diagram of an exemplary computer according to some embodiments of the present disclosure.

FIG. 1 illustrates an application scene schematic diagram of an exemplary imaging system 100 according to some embodiments of the present disclosure. The imaging system 100 may include an imaging device 110, an imaging control device 120, a terminal 130, a display 140, a database 150, and a network 160. In some embodiments, at least a portion of the imaging control device 120 may be implemented by a computer 200 as shown in FIG. 2.

Different components/assemblies in the imaging system 100 may communicate with each other. For example, the imaging control device 120 may be interconnected or communicated with the network 160 or may be directly interconnected or communicated with the imaging system 100 or a portion thereof (e.g., the imaging device 110, the terminal 130), or a combination of both. For example, the imaging control device 120 may transmit data to the terminal 130, obtain one or more user instructions from the terminal 130, send one or more control instructions and the like to the imaging device 110, and exchange data with the database 150, etc. The data communication among the imaging device 110, the imaging control device 120, the terminal 130, the display 140, the database 150, and other devices which may be included in the imaging system 100 may be implemented by a data cable, the network 160, or the like, or a combination thereof.

The imaging device 110 may be used to obtain imaging data. For example, the imaging device 110 may scan a target object and obtain data (e.g., scanning data) associated with the target object. The imaging device 110 may be a single device or a group of devices. In some embodiments, the imaging device 110 may be a medical information collection device, such as a positron emission tomography (PET) device, a single-photon emission computed tomography (SPECT) device, a computed tomography (CT) device, and a magnetic resonance imaging (MRI) device, etc. The device may be used independently or in combination. The imaging device 110 may be a PET-CT device, a PET-MRI device, or a SPECT-MRI device, etc. The scanning data may be data related to the signal data obtained by the imaging device 110 after signal data (e.g., an X-ray signal, a magnetic field signal) emitted from the imaging device 110 passes through an object (e.g., a human body). The scanning data may be CT scanning data, MRI scanning data, ultrasonic scanning data, X-ray scanning data, or the like, or any combination thereof.

The imaging device 110 may generate an image based on the obtained data. For example, the imaging device 110 may generate an image based on the scanning data. The scanning data may be from the imaging device 110 or the database 150. The generated image contains information of the scanned object. The operation of scanning data to generate the image may include data superposition, Fourier transformation, conversion of signal strength into gray value, three-dimensional reconstruction, multimodality fusion, or the like, or any combination thereof. The generated image may be a two-dimensional image (e.g., a section image), a three-dimensional reconstruction image, a four-dimensional reconstruction image, a multimodality image, or the like, or any combination thereof. The generated image may be a grayscale image, a black-and-white image, a binary image, or a color image, etc. In the process of generating the image based on the scanning data, the imaging control device 120 may further use one or more data processing operations, such as a data preprocessing, data conversion processing, data cleaning processing, data fitting processing, data weighting processing, or the like, or any combination thereof.

The imaging device 110 may include a scanning component. The scanning component may scan the target object. The scanning component may be a radioactive scanning device. The radioactive scanning device may include a radioactive source. The radioactive source may emit radioactive rays. The radioactive rays may include a particle ray, a photon ray, or the like, or any combination thereof. The particle ray may include neutrons, protons, a-rays, electrons, p mediums, heavy ions, or the like, or any combination thereof. The photon ray may include X-rays, y-rays, ultraviolet rays, lasers, or the like, or any combination thereof. For example, the photon ray may be X-rays. Accordingly, the imaging device 110 may be a CT system, a digital radiography (DR) system, a multimodality medical imaging system, or the like, or any combination thereof. The multimodality medical imaging system may include a CT-PET system, an SPECT-MRI system, or the like, or any combination thereof. The imaging device 110 may also include a ray detection unit (not shown in FIG. 1) to complete the detection of the generated rays, etc.

The imaging control device 120 may perform imaging control. The imaging control may be control of one or more components or devices of the imaging system 100 (e.g., the scan component in the imaging device 110, the display 140, and the terminal 130). For example, the imaging control device 120 may generate a filament preheating plan, and the imaging device 110 may perform a filament preheating operation based on the filament preheating plan. The imaging control device 120 may control the imaging device 110 by control instructions. The control instructions may be generated based on data generated by the imaging control device 120 or may be generated based on data (e.g., user instructions) obtained from other devices (e.g., the terminal 130). In some embodiments, the imaging control device 120 may generate a control instruction based on one or more user instructions. For example, the control instruction may be an adjustment of one or more parameters of the imaging device 110. The parameters may include a filament preheating time, filament preheating current, tube voltage, tube current, or the like, or any combination thereof. The imaging device 110 may perform operations such as filament preheating based on the control instructions.

In some embodiments, the imaging control device 120 may transmit data to the database 150 or read data from the database 150. The data may be data directly or indirectly obtained from the imaging device 110, temporary or non-temporary data generated by the imaging control device 120, or data for assisting the imaging control device 120 to perform imaging control, etc.

In some embodiments, the imaging control device 120 may be a single computer or a group of computers. The group of computers for implementing the imaging control device 120 may be in wired connection or wireless connection (e.g., via the network 160). The group of computers for implementing the imaging control device 120 may indirectly communicate with each other via one or more devices. The imaging control device 120 may be installed in a same geographic location as the imaging device 110. The imaging control device 120 may be architected in the cloud. In some embodiments, the imaging control device 120 may be a component of the imaging device 110. The terminal 130 may be a component of the imaging device 110 or an independent device.

The terminal 130 may be connected or communicated with the imaging control device 120. The terminal 130 may allow one or more users (e.g., a doctor, an image technician) to control the generation or display of an image (e.g., displayed on the display 140). The terminal 130 may include an input device, an output device, a control panel (not shown in FIG. 1), or the like, or any combination thereof. The input device may include a keyboard, a touch control device, a mouse, keys, an audio input device (e.g., a microphone), an image input device (e.g., a scanner, a camera), a remote control device (e.g., a remote control, a remotely connected computer), a data input device (e.g., an optical drive, a USB port), or the like, or any combination thereof. A user may input user operation data via the input device. The manner in which the user inputs data may include but not limited to a mouse operation, keyboard input, a key operation, a touch control operation, a voice control operation, an expression operation, a somatosensory operation, a neural signal operation, or the like, or any combination thereof. In some embodiments, the user may input information such as instrument parameters, data processing parameters, image display parameters, or the like directly or indirectly to the terminal 130, the imaging control device 120, the imaging device 110 and/or other devices/components which may exist in the imaging system 100 via the input device. The input information may be from external data sources (e.g., a floppy disk, a hard disk, an optical disk, a memory chip, the network 160, or the like, or any combination thereof).

The display 140 may display information. The information may include error information in a filament calibration and a filament preheating process, a filament preheating plan, an emission plan, data used and/or generated in the filament calibration or the filament preheating process, or the like, or any combination thereof. The display 140 may include a liquid crystal display (LCD), a light emitting diode (LED)-based display, a flat panel display or a curved surface display (or a television), a cathode ray tube (CRT), or the like, or any combination thereof.

The database 150 may be used to store data. The stored data may be data generated or obtained by the imaging system 100, such as scanning data, data generated when one or more components of the imaging system 100 operate, data input by the user via the terminal 130, data obtained by the user from other data sources (not shown in FIG. 1) via the network 160, etc. The stored data may include data of the X-ray tube (e.g., tube current, filament current). The database 150 may be a device/component or a combination of multiple devices/components having a memory function. In some embodiments, the database 150 may include one or more independent devices having a data memory function, for example, a computer, a server, etc. The database 150 may include a local memory or a remote memory (e.g., a cloud platform connected to the network 160). In some embodiments, the database 150 may include a component having a data memory function in an independent device, for example, a disk, or a disk array, etc. The database 150 may include components having a memory function of any device in the imaging system 100 (e.g., the imaging device 110, the imaging control device 120, the terminal 130).

In some embodiments, the database 150 may store scanning data. The scanning data may be from the imaging device 110, the terminal 130 (e.g., obtained via a mobile memory device socket), the network 160, etc. For example, the database 150 may store CT scanning data and/or MRI scanning data. In some embodiments, the database 150 may store temporary data/images or non-temporary data/images generated when the imaging control device 120 and/or the terminal 130 are in normal operation. For example, the database 150 may store some system operation temporary files, scanning images, output images, temporary data/images, etc. In some embodiments, the database 150 may store information collected by the terminal 130 from the user or data generated based on the information, for example, user operation data, user input data, user instructions, authentication data, etc.

In some embodiments, the database 150 may store program codes (e.g., software, an operation system) for running the imaging device 110, the imaging control device 120 and/or the terminal 130, etc. The database 150 may also store data of one or more algorithms/models, parameter data, reference data/images, etc. The program code, algorithm/model data, parameter data, standard data and the like may be added to the database 150 by an installer when a program for implementing one or more functions of the imaging system 100 is installed, or added to the database 150 by the user via the terminal 130 or the network 160.

The network 160 may be used to transfer information among various devices/components in the imaging system 100. The network 160 may be an independent network or a combination of various networks. For example, the network 160 may include a local area network (LAN), a wide area network (WAN), a public switched telephone network (PSTN), a virtual network (VN), or the like, or any combination thereof. The network 160 may include a plurality of network access points. The network 160 may use a wired network architecture, a wireless network architecture, and a wired/wireless network hybrid architecture. A wired network may include a metal cable, a hybrid cable, an optical cable, or the like, or any combination thereof. The transmission method of the wireless network may include Bluetooth™, Wi-Fi, ZigBee™, Near Field Communication (NFC), cellular networks (including GSM, CDMA, 3G, 4G), or the like.

It should be noted that the above description of the imaging system 100 is provided merely for illustration, and is not intended to limit the scope of the present disclosure. It may be appreciated that for persons having ordinary skills in the art, after understanding the principle of the system, various changes in details can be made on the imaging system 100, such as any combination of a plurality of devices/assemblies/modules (e.g., the imaging control device 120, the database 150, and the terminal 130 are combined into one device), a split of a single device/assembly/module (e.g., the imaging control device 120 is split into one or more devices for performing one or more functions of the imaging control device 120 respectively), adding devices/assemblies not related to the present invention (e.g., a filtering device) for the imaging system 100, changing the connection between the main devices/assemblies from a direct connection to an indirect connection (e.g., adding one or more signal receiving and transmitting devices and transcoding devices), changing the type of the imaging device 110 so as to apply the system to different fields, etc., however, these changes may not depart from the scope of the claims.

FIG. 2 illustrates a schematic diagram of an exemplary computer 200 according to some embodiments of the present disclosure. The computer 200 may be applied to the imaging system 100, any devices/components included in the imaging system 100 (e.g., the imaging control device 120, the terminal 130), functional modules included in the devices/components (e.g., a calibration module 410, a preheating module 420), functional units included in the functional modules (e.g., a tube current determination unit 412, a preheating time determination unit 423) and the like to implement one or more functions of the system, device, component, module, unit or the like in the present disclosure. The computer 200 may implement one or more functions (e.g., filament calibration, generation of a filament preheating plan) of the imaging system 100 via its hardware device, software program, firmware and combinations thereof. The computer 200 may have a general application scene or a special application scene (e.g., application of generating, processing, displaying medical images). The computer 200 may be a single computer or a group of computers. For convenience, only one computer 200 is shown in FIG. 2, but a function of the imaging system 100 described herein (e.g., scanning data acquisition, data processing, image processing) may be implemented in a distributed manner on some similar computer platforms (parallel or serial) to distribute the processing load.

The computer 200 may include an internal communication bus 210, a central processing unit (CPU) 220, a data memory unit (e.g., a read-only memory (ROM) 230, a random access memory (RAM) 240, a hard disk 250), an I/O component 260, communication (COM) ports 270, etc. The internal communication bus 210 may be used to transfer data between different components of the computer 200. The CPU 220 may be used to execute one or more instructions (including user instructions, program instructions, control instructions) and to assume one or more algorithms (e.g., an interpolation algorithm). The CPU 220 may include a single chip or a group of chips. One or more functions of the imaging control device 120 may be implemented by the CPU 220. The computer 200 may further include a graphics processing unit (GPU) (not shown in FIG. 2) for assisting the CPU 220 in processing graphics data. The graphics processing unit may be an independent component in the computer 200 or may be encapsulated on a same chip as the central processing unit.

The read-only memory 230, the random access memory 240 and the hard disk 250 may store various data files or programs involved in processes such as computer operations, computer communications, computer function implementation, etc. (more detailed description may refer to the related description of database 150 in FIG. 1). The I/O component 260 may support the computer 200 to perform data communication with one or more peripheral devices 280. The I/O component 260 may include one or more connection ports, such as COM ports (communication ports), USB (Universal Serial Bus) ports, HDMI (High-Definition Multimedia Interface) ports, VGA (Video Graphics Array) ports, DVI (Digital Video Interactive) ports, PS/2 interfaces, etc. The peripheral device 280 may perform data communication via the input/output component 260 and the internal communication bus 210. The peripheral device 280 may be a device for input or output, for example, a display, a printer, a mouse, a keyboard, a handle, a touch screen, a camera, a speaker, or the like, or any combination thereof. The peripheral device 280 may include one or more input components and output components in the terminal 130 (more detailed description may refer to the related description of the terminal 130 in FIG. 1). The COM ports 270 may perform data communication via one or more networks (more detailed description may refer to the related description of the network 160 in FIG. 1).

Figure 3:
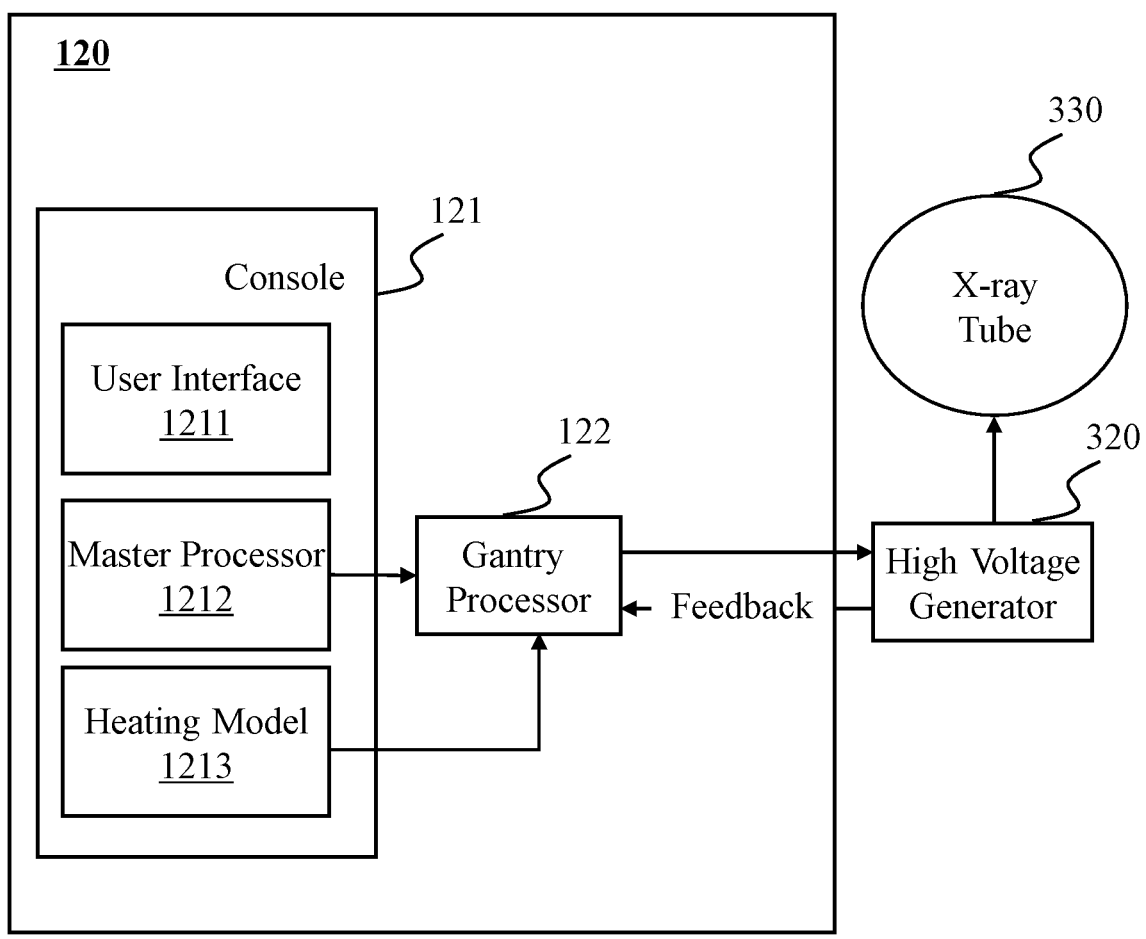
FIG. 3 illustrates a schematic diagram of an exemplary system for X-ray tube filament current control according to some embodiments of the present disclosure.

FIG. 3 illustrates a schematic diagram of an exemplary system 300 for X-ray tube filament current control according to some embodiments of the present disclosure. The system 300 may include an imaging control device 120, a high voltage generator 320, and an X-ray tube 330.

The imaging control device 120 may communicate with the high voltage generator 320. For example, the imaging control device 120 may control the amplitude of the voltage generated by the high voltage generator 320. In some embodiments, the imaging control device 120 may send an instruction to the high voltage generator 320, and the instruction may include a filament preheating instruction, an instruction of an X-ray loading plan, etc. The instruction of the X-ray loading plan may be an instruction to perform an X-ray loading operation. The instruction of the X-ray loading plan may be an instruction including parameters required for X-ray loading (e.g., X-ray loading time, X-ray radiation intensity). Relevant parameters (e.g., X-ray loading time, X-ray radiation intensity) of the X-ray loading may be determined based on the instruction of the X-ray loading plan. The high voltage generator 320 may receive the instruction and perform one or more operations. The operations may include adjusting the amplitude of the voltage generated by the high voltage generator 320, etc. The high voltage generator 320 may feed information back to the imaging control device 120. The information may include information, for example, the voltage amplitude of the high voltage generator 320, etc. The imaging control device 120 may include a console 121, and a gantry processor 122.

One or more components (e.g., a master processor 1212, a heating model 1213) in the console 121 may send information (e.g., filament current information, preheating time information) to the gantry processor 122. The gantry processor 122 may generate an instruction (e.g., a filament preheating instruction) based on the information and send the instruction to the high voltage generator 320. The console 121 may include a user interface 1211, a master processor 1212, and a heating model 1213.

The user interface 1211 may receive setting for a parameter of the imaging system 100 by the user. The parameter may be an emission plan parameter, such as tube voltage, tube current, a start time for emission, etc. For example, the user may set the start time for emission during an emission operation of the imaging system 100 via the user interface 1211.

The master processor 1212 may be used for processing of information. The information may be an emission plan parameter (e.g., tube voltage, tube current, a start time for emission), a heating model, etc. The processing operation may include generating a filament preheating plan, determining a filament preheating time, calibrating the corresponding relationship between the tube current of the filament and the filament current, performing a mathematical operation (e.g., an iterative operation, an interpolation operation), etc.

The master processor 1212 may obtain information from the user interface 1211, the heating model 1213, the database 150, etc. The master processor 1212 may send the processed information to the gantry processor 122 or may save the processed information into the database 150 or other memory devices. The manner of information processing may include storage, classification, calculation, conversion of the information, or the like, or any combination thereof.

In some embodiments, the master processor 1212 may obtain an emission plan from the user interface 1211. The master processor 1212 may generate a filament preheating plan based on the emission plan. The filament preheating plan may include information such as one or more filament preheating currents, and time information corresponding to the one or more filament preheating currents. For example, the filament preheat plan may include preheating with certain filament preheating current (e.g., current of 3.5 A) within a period (e.g., within a period of from 1.0 s to 1.5 s). The filament preheating current may be filament current corresponding to the filament preheating process. The filament current may be determined by the voltage of the filament provided by the high voltage generator 320. The master processor 1212 may send the filament preheating plan to the gantry processor 122. The gantry processor 122 may generate a filament preheating instruction based on the filament preheating plan. The high voltage generator 320 may perform a preheating operation based on the filament preheating instruction.

In some embodiments, the master processor 1212 may perform a calibrating operation of the filament current. The calibrating operation may include calibration of a first calibration point and a second calibration point. The first calibration point may be one or more preset calibration points (e.g., data of tube current and filament current provided by the manufacturer when the X-ray tube left a factory). The second calibration point may be one or more fitting values. Techniques used in the calibration may include an iterative operation technique, a curve fitting technique, an interpolation operation technique, etc.

The heating model 1213 may be used to establish a heating model. The heating model 1213 may be stored in advance in the memory inside or around the master processor 1212. The master processor 1212 may obtain one or more heating models from the heating model 1213. The heating models may include a corresponding relationship of tube voltage, tube current, a time length of preheating of a filament, and filament preheating current. The heating models may exist in the form of a data table and may exist in the form of a function.

Figure 9:
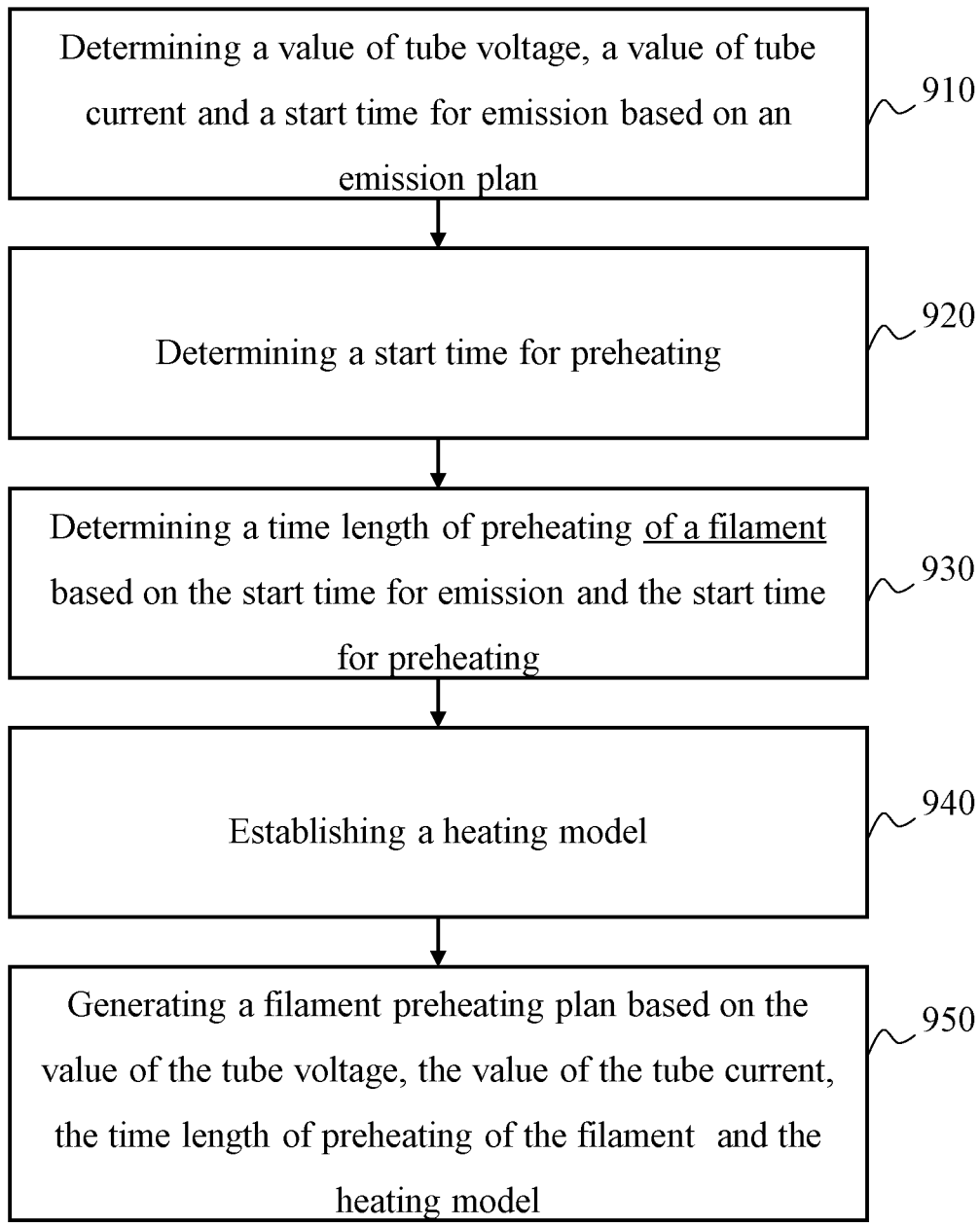
FIG. 9 illustrates a flowchart of an exemplary process for X-ray tube preheating plan generation according to some embodiments of the present disclosure.
Figure 11:
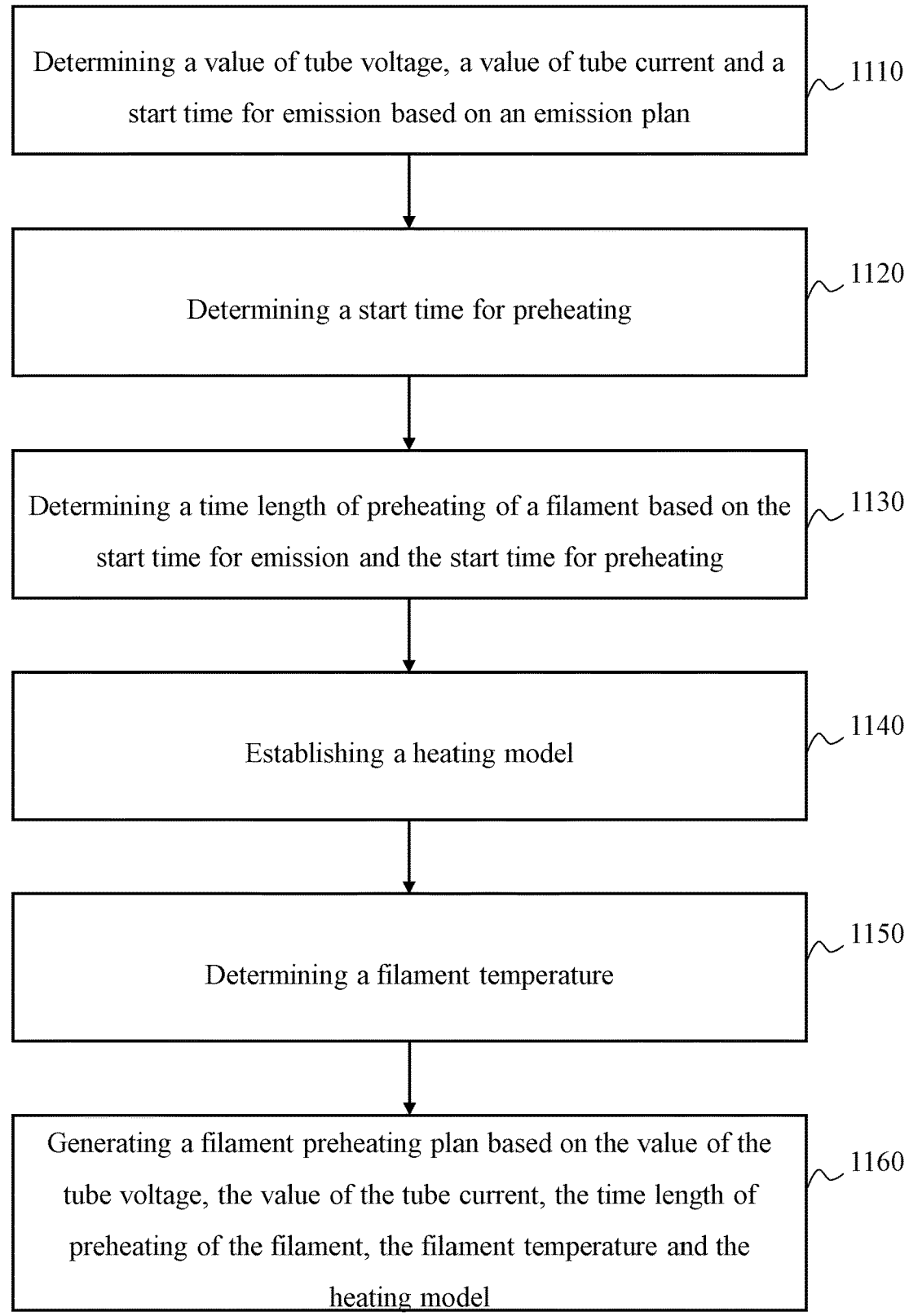

In some embodiments, establishing a model may include determining a model (e.g., performing one or more steps described in 940 of FIG. 9, or performing one or more steps described in 1140 of FIG. 11). In some embodiments, establishing a model may include selecting a heating model from one or more heating models (e.g., selecting one from Table 1 or Table 2 as a heating model). In some embodiments, establishing a model may include reading the model from memory or obtaining the model in other ways.

The high voltage generator 320 may generate a high voltage and provide it to the X-ray tube 330. The high voltage may be applied between a cathode and an anode of the X-ray tube 330. Merely by way of example, the high voltage may be a voltage within a voltage range (e.g., a range from 30 kV to 150 kV). The high voltage generator 320 may also provide a voltage to a cathode filament of the X-ray tube 330. The cathode filament of the X-ray tube 330 may produce filament current under the voltage. Merely by way of example, the filament current may be a value within a current range (e.g., within a range from 3 A to 3.5 A), and the filament current may be a constant value (e.g., 3 A, 4 A, or 6.5 A).

The X-ray tube 330 may generate an X-ray beam. The X-ray tube 330 may be a cold cathode tube, a high vacuum hot cathode tube, a rotating anode tube, etc. The shape of the X-ray beam may include a line shape, a pencil shape, a sector shape, a cone shape, a wedge shape, an irregular shape, or the like, or any combination thereof. The X-ray tube 330 may include a cathode, an anode and a housing (not shown in FIG. 3). The cathode may emit electrons. The anode may accept electron bombardment and produce an X-ray beam. The anode and the cathode may be sealed in the housing. The housing may provide a vacuum environment to ensure that the electron movement is not blocked. The housing may consist of heat-resistant glass or a metal frame. The cathode may include a filament. The filament may be composed of a high melting point metal material (e.g., tungsten). When the filament current flows through the filament, the filament may be heated to release electrons. The electrons may be capable of impacting the anode at high speed under the action of a high voltage between the cathode and the anode. After the electrons reach the anode, the movement may be blocked and energy conversion occurs, and a part of kinetic energy of the electron may be converted into radiant energy. The radiant energy may be released in the form of an X-ray beam. The high voltage electric field between the cathode and the anode may be referred to as tube voltage. The current formed by the high-speed movement of the electrons between the cathode and the anode may be referred to as tube current. The region which absorbs electrons and produces X-ray on the anode target surface may be referred to as a focal point.

Figure 4:
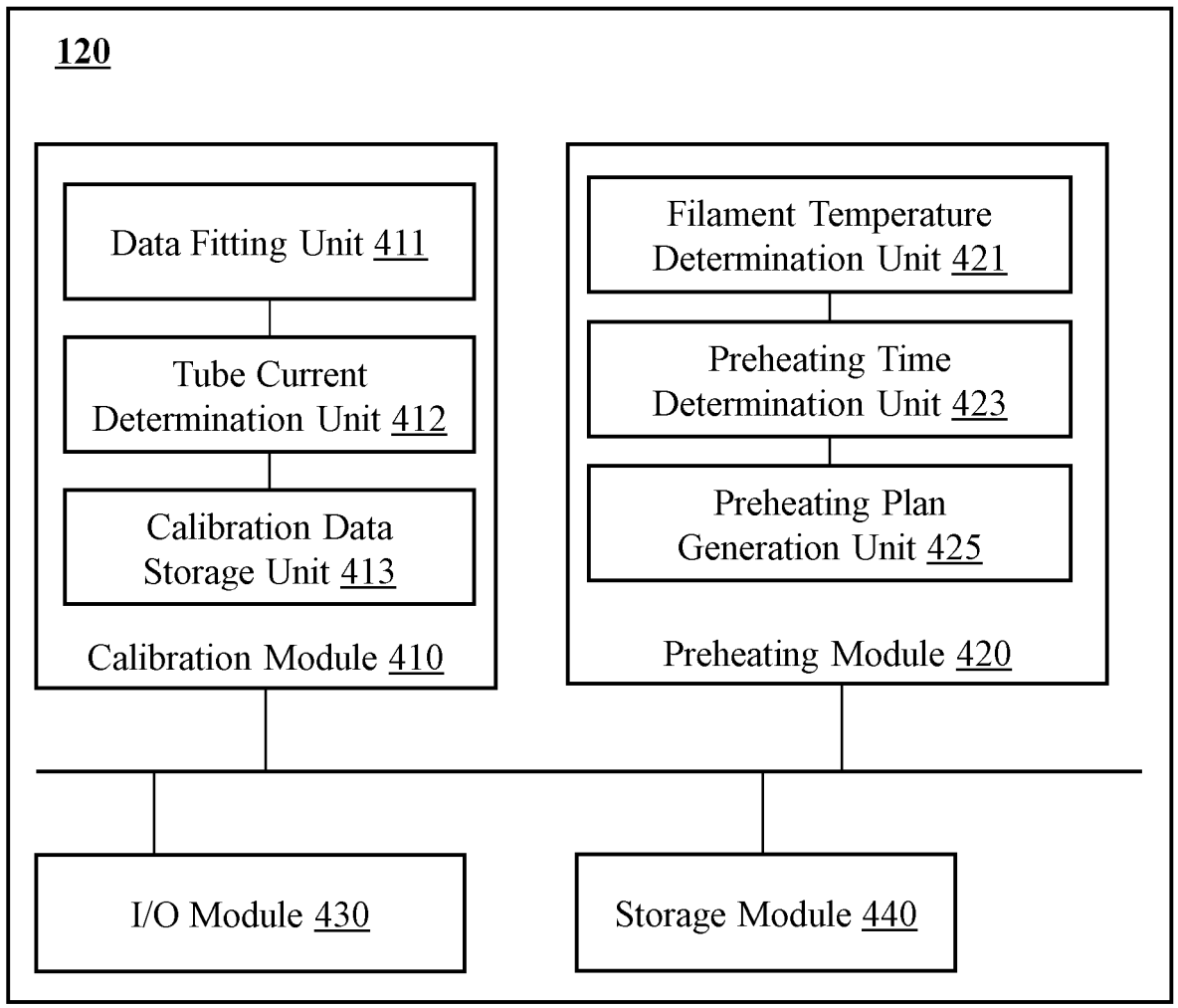
FIG. 4 illustrates a module diagram of an exemplary imaging control device according to some embodiments of the present disclosure.

FIG. 4 illustrates a module diagram of an exemplary imaging control device 120 according to some embodiments of the present disclosure. The imaging control device 120 may include a calibration module 410, a preheating module 420, an I/O module 430, and a storage module 440.

The calibration module 410 may perform a filament calibration operation. The filament calibration operation may include calibrating a corresponding relationship between tube current and filament current. The calibration operation may include determining filament current calibration data. The calibration operation may also include data fitting based on the filament current calibration data. The calibration operation may generate third filament current calibration data corresponding to the third value of tube voltage based on first filament current calibration data corresponding to a first value of the tube voltage and second filament current calibration data corresponding to a second value of the tube voltage. Techniques used in the filament calibration operation may include an iterative operation technique, a curve fitting technique, an interpolation operation technique, etc. The curve fitting technique may include a least square method, etc. The interpolation operation technique may include a Lagrange interpolation algorithm, a Newton interpolation algorithm, a Hermite interpolation algorithm, etc.

The calibration module 410 may include a data fitting unit 411, a tube current determination unit 412, and a calibration data storage unit 413.

The data fitting unit 411 may perform a data fitting operation. The data fitting operation may be completed based on any data associated with the imaging system 100. For example, the data may include tube current, filament current, a focal point size, tube voltage, etc. The data fitting operation may include determining the corresponding relationship between the tube current and the filament current at a specific focal point size and a value of the tube voltage. The data fitting unit 411 may fit the data using one or more data fitting techniques. The data fitting techniques may include a linear fitting technique, a curve fitting technique, etc. For example, the data fitting technique may be a least square method, etc.

The data fitting unit 411 may determine one or more second calibration points based on a fitting result. The second calibration point may be a calibration point for the value of the tube current within a current value interval (e.g., a current value interval outside a first tube current value interval). For example, Table 1 shows a case of focal point size 1 and tube voltage of 70 kV, the second calibration point may be a calibration point corresponding to the value of the tube current outside an interval from 30 mA to 300 mA. For example, calibration points corresponding to values of the tube current of 10 mA, 400 mA, 500 mA, and 600 mA.

The tube current determination unit 412 may determine an actual value of the tube current. The actual value of the tube current may be a value of the tube current corresponding to a specific time (e.g., a time point, a time period), or may be a value (e.g., an average value of values of the tube current at a plurality of times) calculated based on values of the tube current of a plurality of times (e.g., a plurality of time points, a plurality of time periods). The actual value of the tube current may be an actual value of the tube current in an emission process or actual values of the tube current in a plurality of emission processes. For example, in an emission process, a value of the tube current at T1 time is a first value (e.g., mA1), a value of the tube current at T2 time is a second value (e.g., mA2), and a value of the tube current at T3 time is a third value (e.g., mA3). In some embodiments, the actual value of the tube current may be the first value (mA1), the second value (mA2), and/or the third value (mA3). In some embodiments, the actual value of the tube current may also be an average value of the first value (mA1), the second value (mA2), and the third value (mA3).

The calibration data storage unit 413 may store one or more calibration data. The calibration data may include calibration point data and filament current calibration data. The calibration point data may include a set of one or more calibration points. The calibration point may include a focal point size, a value of tube voltage, a value of tube current, filament current, etc. The calibration point may be a default point or a fitting point. The default point may be a calibration point corresponding to a value of the tube current within a default range (e.g., 30 mA to 300 mA shown in Table 1). Data of the default point may be preset data (e.g., data provided by the manufacturer when the X-ray tube leaves factory). The interpolation point may be a calibration point corresponding to a value range of the tube current outside the default range. The interpolation point may also include a maximum endpoint and a minimum endpoint (e.g., a fitting point in Table 1). The interpolation point may be a calibration point obtained based on the data fitting result. The filament current calibration data may correspond to a calibration point, including a tube current datum and a filament current datum.

In some embodiments, the calibration point data may include one or more data as shown in Table 1. The calibration point data in Table 1 may correspond to a specific value of the filament current (e.g., 10 mA). The calibration point data in Table 1 may include a focal point size, a value of tube voltage, and a value of tube current. In some embodiments, a focal point size may correspond to a plurality of tube voltage data. For example, focal point size 1 may correspond to a plurality of values of the tube voltage, which are 10 kV, 80 kV, 100 kV, 120 kV, and 140 kV respectively. In some embodiments, tube voltage may correspond to a plurality of tube current data. For example, as shown in Table 1, value of the tube voltage of 70 kV may correspond to a plurality of values of the tube current, which are 6 mA, 10 mA, 30 mA, 60 mA, 120 mA, 200 mA, 300 mA, 400 mA, 500 mA, 600 mA, and 610 mA respectively.

TABLE 1

Calibration Point Data corresponding to Specific Filament Currents, different Focal Point Sizes and different Values of the Tube Voltage.

| Tube Current (mA) | Focal Point Size 1 | | | | | Focal Point Size 2 | | | | |
| --- | --- | --- | --- | --- | --- | --- | --- | --- | --- | --- |
| | Tube Voltage (kV) | | | | | | | | | |
| | 70 kV | 80 kV | 100 kV | 120 kV | 140 kV | 70 kV | 80 kV | 100 kV | 120 kV | 140 kV |
| Endpoint (Fitting Point) | 6 | 6 | 6 | 6 | 6 | 6 | 6 | 6 | 6 | 6 |
| Interpolation Point (Fitting Point) | 10 | 10 | 10 | 10 | 10 | 10 | 10 | 10 | 10 | 10 |
| Default Point | 30 | 30 | 30 | 30 | 30 | 30 | 30 | 30 | 30 | 30 |
| | 60 | 60 | 60 | 60 | 60 | 60 | 60 | 60 | 60 | 60 |
| | 120 | 120 | 120 | 120 | 120 | 100 | 100 | 100 | 100 | 100 |
| | 200 | 200 | 200 | 200 | 200 | 140 | 150 | 150 | 150 | 150 |
| | 300 | 300 | 300 | 300 | 300 | 180 | 200 | 220 | 220 | 220 |

TABLE 1-continued

Calibration Point Data corresponding to Specific Filament Currents, different Focal Point Sizes and different Values of the Tube Voltage.

| | Focal Point Size 1 | | | | | Focal Point Size 2 | | | | |
| --- | --- | --- | --- | --- | --- | --- | --- | --- | --- | --- |
| | Tube Voltage (kV) | | | | | | | | | |
| Tube Current (mA) | 70 kV | 80 kV | 100 kV | 120 kV | 140 kV | 70 kV | 80 kV | 100 kV | 120 kV | 140 kV |
| Interpolation Point (Fitting Point) | 400 | 400 | 450 | 400 | 400 | 220 | 250 | 280 | 300 | 310 |
| | 500 | 530 | 600 | 550 | 600 | | | | | |
| | 600 | 670 | 770 | 700 | | | | | | |
| Endpoint (Fitting Point) | 610 | 680 | 780 | 833 | 714 | 230 | 260 | 290 | 310 | 320 |

The preheating module 420 may generate a filament preheating plan. The filament preheating plan may include information such as one or more filament preheating current values and time information corresponding to the one or more filament preheating current values. The operation of generating the filament preheating plan may include determining a filament temperature, determining a preheating time length, building a heating model, etc. The preheating module 420 may include a filament temperature determination unit 421, a preheating time determination unit 423, and a preheating plan generating unit 425.

The filament temperature determination unit 421 may determine a filament temperature. Determination of the filament temperature may be determining an initial value of the filament temperature. Determination of the filament temperature may be determining an equivalent description value of the filament temperature. The equivalent description value of the filament temperature may describe the thermionic emission capability of a filament, such as thermionic energy, energy level, the surface barrier of the filament, etc. In some embodiments, the filament temperature determination unit 421 may determine the filament temperature based on a value of tube voltage of a first emission, a value of tube current of the first emission, an end time for the first emission, a start time for a second emission, and/or a heating model (e.g., a filament heat dissipation table). The heating model may include the corresponding relationship between the filament temperature and an emission time interval at a value of the tube voltage and a value of the tube current of the first emission. For example, the heating model may exist in the form of a filament heat dissipation table shown in Table 5 (see details of the description of FIG. 11). As another example, the heating model may exist in the form of a function. The emission time interval may include a time interval between an end time for the first emission and a start time for the second emission. In some embodiments, the filament temperature determination unit 421 may directly obtain the filament temperature from the imaging device 110. For example, the imaging system 100 may include a thermometer for measuring the filament temperature. The filament temperature determination unit 421 may obtain the filament temperature from the thermometer.

The preheating time determination unit 423 may determine preheating time information. The preheating time information may include a start time for preheating, an end time for preheating, a start time for emission, an end time for emission end time, a time length of preheating of a filament, etc. The time length of preheating of the filament may be a time difference from the start time for preheating to the start time for emission. The preheating time determination unit 423 may determine the start time for emission based on an emission plan.

The preheating plan generation unit 425 may generate a filament preheating plan. In some embodiments, the preheating plan generation unit 425 may generate the filament preheating plan based on a value of tube voltage, a value of tube current, a time length of preheating of a filament, and a heating model. In some embodiments, the preheating plan generation unit 425 may generate the filament preheating plan based on a value of tube voltage, a value of tube current, a time length of preheating of a filament, a filament temperature, and a heating model. In some embodiments, the preheating plan generation unit 425 may generate the filament preheating plan based on a difference between a value of tube current of a first emission and a value of tube current of a second emission, and a heating model. In some embodiments, the preheating plan generation unit 425 may determine whether to modify the filament preheating plan based on whether an instruction of an X-ray loading plan is received.

The I/O module 430 may receive information from one or more other modules or components of the imaging system 100 (e.g., the calibration module 410, the preheating module 420, the storage module 440, and the database 150), and send the information to one or more other modules or components of the imaging system 100. The form of the information may include text, audio, a video, a picture, or the like, or any combination thereof. In some embodiments, the I/O module 430 may include a keyboard, a mouse, a display, or the like, or any combination thereof.

The storage module 440 may store data. The stored data may be data generated or obtained by the imaging control device 120, for example, filament preheating current data, data produced by one or more modules of the imaging control device 120 when operating, data from the database 150 input through the I/O module 430, etc. In some embodiments, the storage module 440 may be incorporated into the calibration module 410 and/or the preheating module 420, or the database 150 of FIG. 1.

It should be noted that the above description of the imaging control device 120 is provided merely for the purpose of illustration, and is not intended to limit the scope of the present disclosure. It may be appreciated that for persons having ordinary skills in the art, after understanding the principle of the system, various modifications and changes in forms and/or various details can be made on the imaging control device 120, however, these modifications and changes may not depart from the scope disclosed by the present disclosure. For example, the imaging control device 120 may include some other components, for example a communication interface, a power supply, etc. For example, the storage module 440 may be omitted from the imaging control device 120 and/or incorporated into the database 150 of FIG. 1. For example, the calibration data storage unit 413 may be incorporated into the storage module 440.

Figure 5:
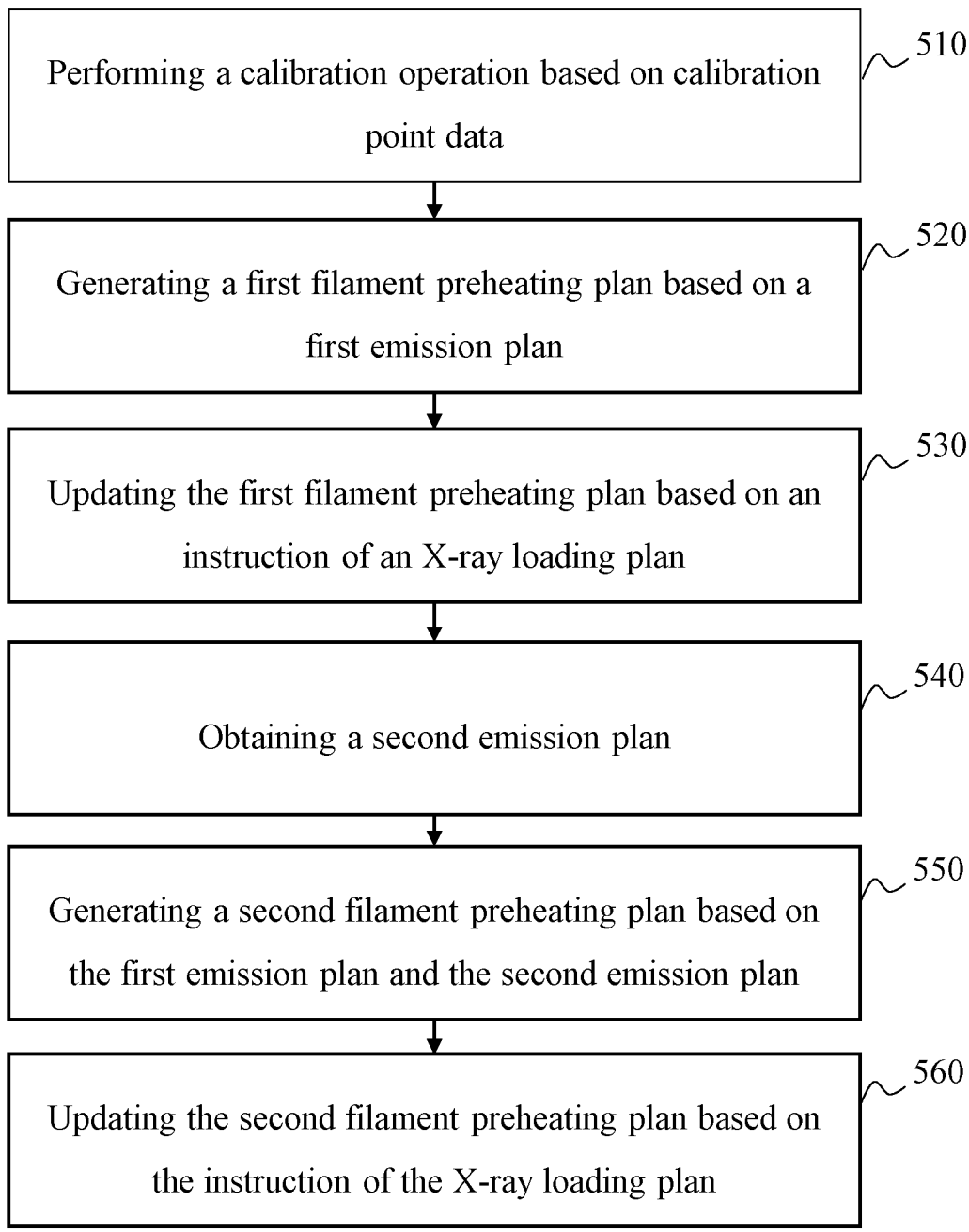
FIG. 5 illustrates a flowchart of an exemplary process for X-ray tube filament current control according to some embodiments of the present disclosure.

FIG. 5 illustrates a flowchart of an exemplary process 500 for X-ray tube filament current control according to some embodiments of the present disclosure. In some embodiments, one or more operations in process 500 may be implemented by the imaging control device 120.

In 510, the process 500 may perform a calibration operation based on calibration point data. The calibration operation may be implemented by the calibration module 410. The calibrating operation may be generating filament current calibration data based on the calibration point data. The calibration point data may include data regarding one or more calibration points. The calibration point data may include a focal point size, a value of tube voltage, a value of filament current, a value of tube current, etc. In some embodiments, the calibration point data may be as shown in Table 1 (more details about Table 1 may be described with reference to FIG. 4). The techniques used in the calibrating operation may include an iterative operation technique, a curve fitting technique, an interpolation operation technique, etc.

In 520, the process 500 may generate a first filament preheating plan based on a first emission plan. The operation of generating the first filament preheating plan may be implemented by the preheating module 420. The first emission plan may include a value of tube voltage of a first emission, a value of tube current of the first emission, a start time for emission of the first emission, an end time for emission of the first emission, etc. The first emission plan may be obtained from the I/O module 430, the storage module 440, etc. The first filament preheating plan may include information such as one or more filament preheating current values, and time information corresponding to the one or more filament preheating current values.

In 530, the process 500 may update the first filament preheating plan based on an instruction of an X-ray loading plan. The operation of updating the first filament preheating plan may be implemented by the preheating module 420. The updating operation may include modifying one or more parameters in the first filament preheating plan, for example, extending a preheating time. The update may include determining an increased preheating time and determining a corresponding preheating current after the first filament preheating plan ends. In some embodiments, updating the first filament preheating plan may include performing one or more operations involved in the related description of FIG. 10.

In some embodiments, the imaging control device 120 may determine whether the instruction of the X-ray loading plan is received. If the instruction of the X-ray loading plan is received, the imaging system 100 may execute the instruction of the X-ray loading plan. If the instruction of the X-ray loading plan is not received, the imaging system 100 may modify the first filament preheating plan.

In 540, the process 500 may obtain a second emission plan. The second emission plan may include a value of tube voltage of a second emission, a value of the tube current of the second emission, a start time for emission of the second emission, an end time for emission end time of the second emission, etc.

In 550, the process 500 may generate a second filament preheating plan based on the first emission plan and the second emission plan. The operation of generating the second filament preheating plan may be implemented by the preheating module 420. The second filament preheating plan may include information such as one or more filament preheating currents, and time information corresponding to the one or more filament preheating current. In some embodiments, a filament temperature may be determined based on the first emission plan and the second filament preheating plan. The second filament preheating plan may be generated based on the filament temperature and the second emission plan. For example, generating the second filament preheating plan may include performing one or more operations involved in the related description of FIG. 11. In some embodiments, the second filament preheating plan may be generated based on a difference between the value of the tube current of the second emission and the value of the tube current of the first emission. For example, generating the second filament preheating plan may include performing one or more operations involved in the related description of FIG. 12.

In 560, the process 500 may update the second filament preheating plan based on the instruction of the X-ray loading plan. The operation of updating the second filament preheating plan may be implemented by the preheating module 420. The update of the second filament preheating plan may adopt the method described in step 530.

In some embodiments, a determination whether the instruction of the X-ray loading plan is received may be performed in step 530 and/or step 560. If the instruction of the X-ray loading plan is received, the imaging system 100 may perform an emission operation. During the emission operation, in order to maintain the value of the tube current in the vicinity of a target value of tube current in the emission process, an actual value of the tube current may be monitored in the emission process. The difference between the actual value of the tube current and the target value of the tube current may be obtained in the monitoring. Filament current in the emission process may be adjusted by a filament current control circuit based on the difference. By adjusting the filament current, the difference may be controlled in a threshold range, so as to maintain the value of the tube current in the emission process in the vicinity of the target value of the tube current.

It should be noted that the above description of the process 500 is provided merely for illustration, and is not intended to limit the scope of the present disclosure. It may be appreciated that for persons having ordinary skills, after understanding the principle of the system, various modifications and changes in forms and details may be made on the specific ways and steps of the process 500, however, those modifications and changes may not depart from the scope of the claims of the present disclosure. In some embodiments, several steps in process 500 may be omitted, for example, step 510 and step 530 may be omitted.

Figure 6:
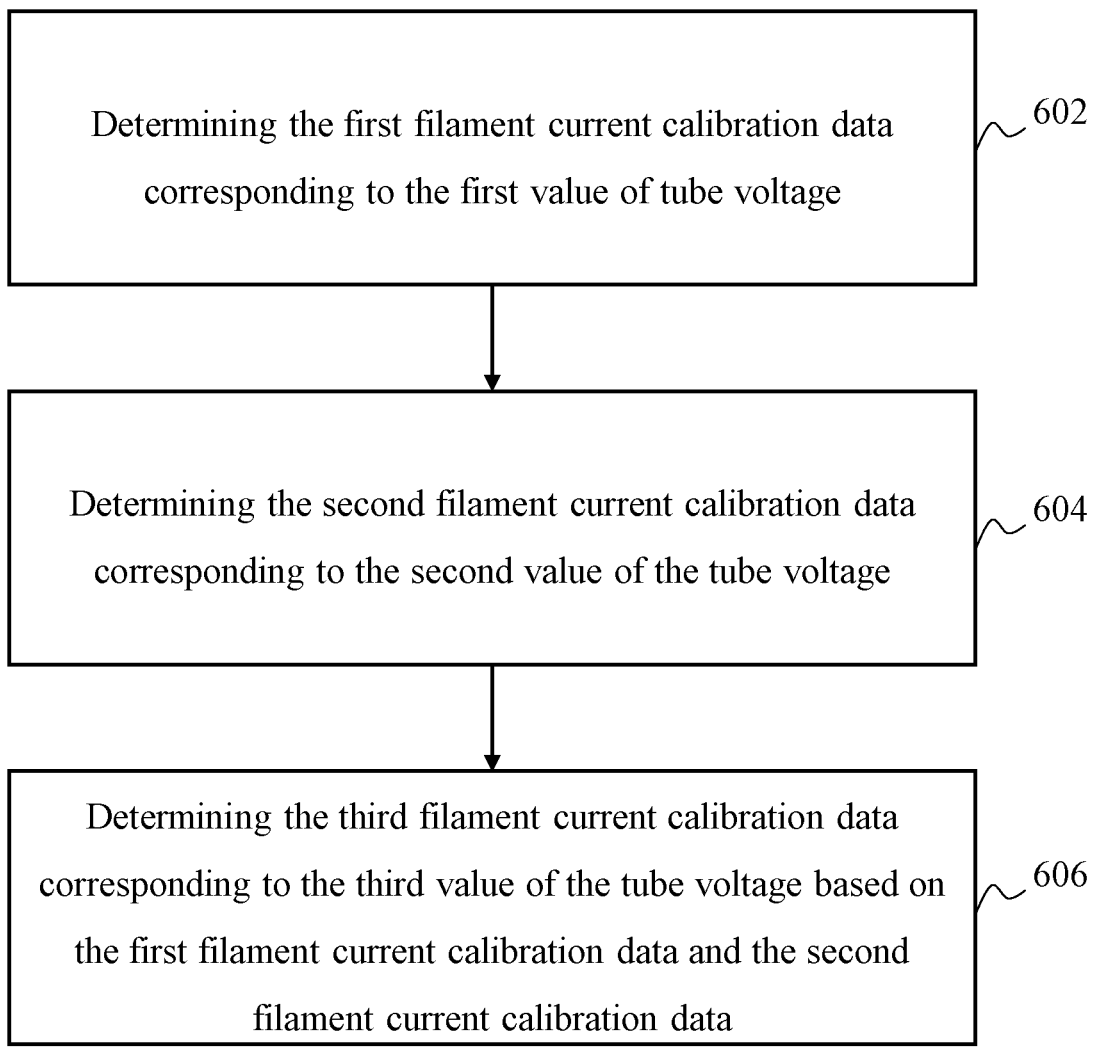
FIG. 6 illustrates a flowchart of an exemplary process for X-ray tube filament calibration according to some embodiments of the present disclosure.

FIG. 6 illustrates a flowchart of an exemplary process 600 for X-ray tube filament calibration according to some embodiments of the present disclosure. One or more operations in the process 600 may be implemented by the imaging control device 120.

In 602, the process 600 may determine the first filament current calibration data corresponding to the first value of tube voltage. The operation of determining the first filament current calibration data may be implemented by the calibration module 410. The first filament current calibration data may include filament current calibration data corresponding to one or more calibration points. The calibration points may be default points or interpolation points. The first filament current calibration data may include a first value of the tube voltage, a value of tube current, a value of filament current, a focal point size, etc. The value of the tube current may include a value of tube current of a first calibration point, a value of tube current of a second calibration point. The first calibration point may include a calibration point of which the value of the tube current is within a default current range (e.g., 30 mA to 300 mA). The second calibration point may be a calibration point of which the value of the tube current is outside the default range. The calibration points may include information of the value of the tube current, the value of the filament current, the value of tube voltage, the focal point size, etc. In some embodiments, the first filament current calibration data may correspondingly include fourth filament current calibration data, the fifth filament current calibration data, and sixth filament current calibration data in FIG. 7.

In 604, the process 600 may determine the second filament current calibration data corresponding to the second value of the tube voltage. The determination operation of the second filament current calibration data may be implemented by the calibration module 410. The second value of the tube voltage may be not equal to the first value of tube voltage in step 602. The determination of the second filament current calibration data may be performed by using a method same as that described in step 602.

In 606, the process 600 may determine the third filament current calibration data corresponding to the third value of the tube voltage based on the first filament current calibration data and the second filament current calibration data. The operation of determining the third filament current calibration data may be implemented by the calibration module 410. The determination of the third filament current calibration data may be performed based on an interpolation algorithm (e.g., a linear interpolation algorithm). For example, filament current calibration data corresponding to tube voltage of 80 kV may be determined by using the linear interpolation algorithm based on the filament current calibration data corresponding to the tube voltage of 70 kV and the tube voltage of 100 kV.

It should be noted that the above description of the process 600 is provided merely for illustration, and is not intended to limit the scope of the present disclosure. It may be appreciated that for persons having ordinary skills in the art, after understanding the principle of the system, changes can be made on the process 600, and various modifications and changes in forms and details of the application of performing the above-mentioned control flow can be made without departing from the scope of the principle. For example, the order of the steps may be adjusted, or some steps may be added or removed. For example, a step of determining seventh filament current calibration data corresponding to a fourth tube voltage may be added between step 604 and step 606. In step 606, the third filament current calibration data corresponding to the third value of the tube voltage may be determined based on the first filament current calibration data, the second filament current calibration data, and the seventh filament current calibration data.

Figure 7:
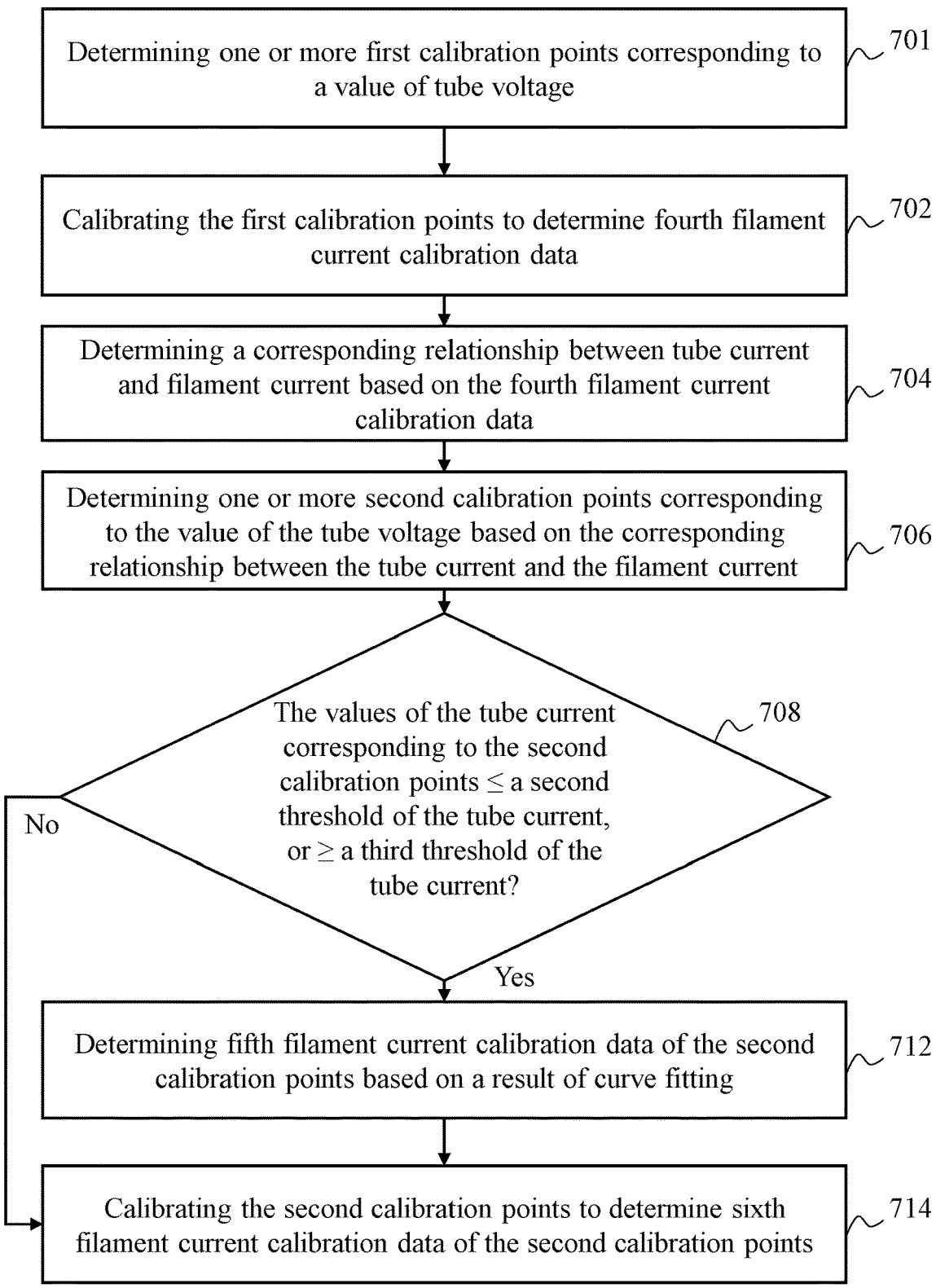
FIG. 7 illustrates a flowchart of an exemplary process for X-ray tube filament calibration according to some embodiments of the present disclosure.

FIG. 7 illustrates a flowchart of an exemplary process 700 for X-ray tube filament calibration according to some embodiments of the present disclosure. One or more operations in the process 700 may be implemented by the imaging control device 120. Specifically, in some embodiments, one or more operations in the process 700 may be implemented by the calibration module 410. In some embodiments, step 602 and/or step 604 in FIG. 6 may be implemented by performing one or more operations in the process 700.

In 701, the process 700 may determine one or more first calibration points corresponding to a value of tube voltage. Values of tube current of the first calibration points may be in a first range. The first range may be a default range of a value of the tube current. The default range may be a data range designated by a user or may be a data range calculated by an imaging system. The default range may be a continuous current range (e.g., from 30 mA to 300 mA), or a set of discrete current values (e.g., a set of 30 mA, 60 mA, 120 mA, 200 mA, and 300 mA). In some embodiments, the first calibration points may be default points in Table 1.

In 702, the process 700 may calibrate the first calibration points to determine fourth filament current calibration data. In some embodiments, the default points may be calibrated according to the method shown in FIG. 8 to generate the fourth filament current calibration data. For example, in a case of focus point size 1 and tube voltage of 70 kV in Table 1, the calibration points corresponding to values of the tube current of 30 mA, 60 mA, 12 mA, 200 mA, and 300 mA may be calibrated according to the method shown in FIG. 8 to generate the fourth filament current calibration data.

In 704, the process 700 may determine a corresponding relationship between tube current and filament current based on the fourth filament current calibration data. The corresponding relationship may be determined by a data fitting technique. The data fitting technique may include a linear fitting technique, a curve fitting technique, etc. Specifically, the curve fitting technique may include a least square method.

Specifically, in some embodiments, the operation of determining the corresponding relationship may be implemented by the data fitting unit 411. The process 700 may determine the relationship between the filament current and the tube current by curve fitting based on the fourth filament current calibration data.

In 706, the process 700 may determine one or more second calibration points corresponding to the value of the tube voltage based on the corresponding relationship between the tube current and the filament current. The second calibration point may correspond to a value of the tube current, a value of the filament current, a value of the tube voltage, a focal point size, etc.

The values of the tube current of the second calibration points may be outside the first range. For example, the first range may be from 30 mA to 300 mA, and the values of the tube current of the second calibration points may be 20 mA. The second calibration points may be interpolation points and/or endpoints based on the values of the tube current of the second calibration points. The interpolation points may be one or more calibration points corresponding to a value of the tube current in the second range and outside the first range. For example, as shown in Table 1, the first range may be from 30 mA to 300 mA, and the corresponding second range may be from 8 mA to 25 mA or from 400 mA to 600 mA, so that the interpolation points may be calibration points corresponding to the tube current of which the values are 10 mA, 400 mA, 500 mA, and 600 mA. The endpoints may be a calibration point corresponding to a maximum and/or minimum value of the tube current in one or more calibration points corresponding to the tube voltage. For example, as shown in Table 1, if the values of the tube current corresponding to a focal point size 1 and tube voltage of 70 kV are 6 mA, 10 mA, 400 mA, 500 mA, and 600 mA, the endpoints may be calibration points corresponding to values of the tube current of 6 mA and 600 mA.

Specifically, in some embodiments, the operation of determining the second calibration points may be implemented by the data fitting unit 411. A value of the filament current corresponding to a value of the tube current at a specific value of the tube voltage and focal point size may be determined based on a result of the data fitting (e.g., a fitting function of the relationship between the filament current and the tube current). A second calibration point may be determined based on the value of the tube current and the value of the filament current.

In 708, the process 700 may determine whether the values of the tube current corresponding to the second calibration points are satisfied with a preset condition. The preset condition may be that the values of the tube current are equal to or smaller than a second threshold of the tube current, or equal to or larger than a third threshold of the tube current. The second threshold of the tube current may be a minimum value of the tube current. The third threshold of the tube current may be a maximum value of the tube current. If the values of the tube current exceed the maximum value, overcurrent may exist. The second threshold of the tube current and the third threshold of the tube current may be a default setting of the imaging system 100, an empirical value, a value of the tube current set by a user (e.g., a doctor), etc. If the values of the tube current corresponding to the second calibration points are satisfied with the preset condition, the process 700 may proceed to step 712. If the values of the tube current corresponding to the second calibration points are not satisfied with the preset condition, the process 700 may proceed to step 714.

In 712, the process 700 may determine fifth filament current calibration data of the second calibration points based on the corresponding relationship between the tube current and the filament current. The second calibration points may be endpoints. The endpoints may include calibration points at which a condition being equal to or smaller than the second threshold of the tube current or equal to or larger than the third threshold of the tube current is satisfied. The fifth filament current calibration data may be determined by calculating the value of the tube current and the value of the filament current based on the corresponding relationship between the tube current and the filament current. In some embodiments, in order to avoid overcurrent, the fitting result may be directly determined to be the fifth filament current calibration data of the endpoints. For example, in a case of focal point size 1 and a value of tube voltage of 70 kV, the second calibration points may be calibration points corresponding to values of the tube current of 6 mA and 610 mA in Table 1. The fitting data corresponding to the calibration points corresponding to the values of the tube current of 6 mA and 610 mA may be taken as the fifth filament current calibration data.

In 714, the process 700 may calibrate the second calibration points to determine sixth filament current calibration data of the second calibration points. The second calibration points may be interpolation points. The interpolation points may be calibration points which are not satisfied with the condition in step 708. In some embodiments, in step 714, the interpolation points may be calibrated by using the method shown in FIG. 8 to determine the sixth filament current calibration data. For example, in a case of focal point size 1 and tube voltage of 70 kV in Table 1, the calibration points corresponding to values of the tube current of 10 mA, 400 mA, 500 mA, and 600 mA may be calibrated according to the method shown in FIG. 8 to generate the sixth filament current calibration data.

In some embodiments, the steps 708 through 714 may be performed cyclically until all the second calibration points are determined. The filament current calibration data of a plurality of calibration points (e.g., the first calibration points, the second calibration points) corresponding tube voltage may be generated based on the fourth filament current calibration data determined in step 702, the fifth filament current calibration data determined in step 712, and the sixth filament current calibration data determined in step 714.

Figure 8:
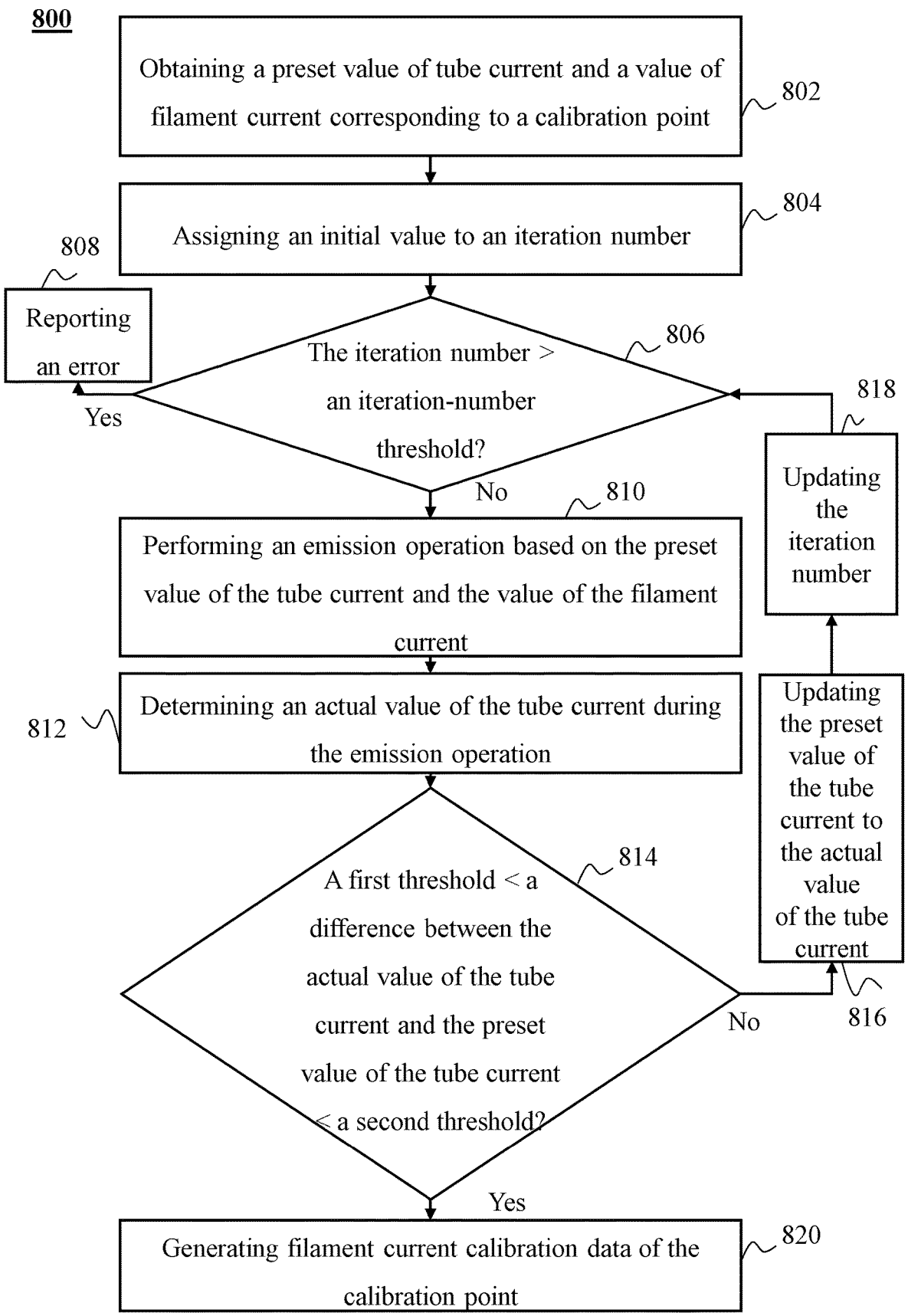
FIG. 8 illustrates a flowchart of an exemplary process for filament current calibration data generation corresponding to a calibration point of according to some embodiments of the present disclosure.

FIG. 8 illustrates a flowchart of an exemplary process 800 for filament current calibration data generation corresponding to a calibration point according to some embodiments of the present disclosure. One or more operations in the process 800 may be implemented by the imaging control device 120. Specifically, in some embodiments, one or more operations in the process 800 may be implemented by the calibration module 410. In some embodiments, step 702 and step 714 in FIG. 7 may be implemented by performing one or more operations in the process 800.

In 802, the process 800 may obtain a preset value of tube current and a value of filament current corresponding to a calibration point. The preset value of the tube current and the preset value of the filament current corresponding to the calibration point may be obtained by the I/O module 430, the storage module 440, etc.

The calibration point may be a known calibration point. For example, the calibration point may be a factory setting parameter. The calibration point may be a calibration point obtained by calculation. For example, the calibration point may be a calibration point obtained by a data fitting technique. The calibration point may be a calibration point corresponding to a value of tube current in any range. For example, the calibration point may be the first calibration points and/or the second calibration points in FIG. 7.

In 804, the process 800 may assign an initial value to an iteration number. The initial value may be 0 or an integer equal to or larger than 0. The iteration number may represent the times that the preset value of the tube current is updated to an actual value of the tube current.

In 806, the process 800 may determine whether the iteration number is larger than an iteration-number threshold. The iteration-number threshold may be a number calculated by the imaging system 100, or a value set by a user, etc. If the iteration number is larger than the iteration-number threshold, the process 800 may proceed to step 808. If the iteration number is not larger than the iteration-number threshold, the process 800 may proceed to step 810.

In 808, the process 800 may report an error. The reporting form of the error may be a literal form, a voice form, an image form, etc. The error may be sent to the terminal 130 or displayed on the display 140.

In 810, the process 800 may perform an emission operation based on the preset value of the tube current and the value of the filament current. The emission operation may be implemented by the imaging device 110. In some embodiments, the emission operation process may include making a filament preheating plan.

In 812, the process 800 may determine an actual value of the tube current during the emission operation. The actual value of the tube current may be a value of the tube current at a specific time (e.g., a time point, a time segment), or a value obtained by calculation based on values of the tube current at a plurality of times during the emission operation (e.g., an average of the values of the tube current at a plurality of times). The emission operation may be one emission operation or a plurality of emission operations. For example, during an emission operation, a value of the tube current at time T1 is a first value (e.g., mA1), a value of the tube current at time T2 is a second value (e.g., mA2), and a value of the tube current at time T3 is a third value (e.g., mA3). In some embodiments, the actual value of the tube current may be the first value (mA1), the second value (mA2), and/or the third value (mA3). In some embodiments, the actual value of the tube current may also be an average of the first value (mA1), the second value (mA2), and the third value (mA3).

In 814, the process 800 may determine whether a difference between the actual value of the tube current and the preset value of the tube current is satisfied with a preset condition. The preset condition may include that the difference is larger than a first threshold and smaller than a second threshold. If the difference is satisfied with the condition, the process 800 may proceed to step 820. If the difference is not satisfied with the condition, the process 800 may proceed to step 816. The first threshold and the second threshold may be values calculated by the imaging system 100, and may also be values set by a user. The first threshold and the second threshold each may be any value. The absolute values of the first threshold and the second threshold may be equal or not. For example, the first threshold may be −1 mA, and the second threshold may be 1 mA. As another example, the first threshold may be −1 mA, and the second threshold may be 2 mA.

In 820, the process 800 may generate filament current calibration data of the calibration point. The filament current calibration data of the calibration point may include the calibrated value of the filament current, the calibrated value of the tube current, the value of the tube voltage and the focal point size corresponding to the calibration point.

In 816, the process 800 may update the preset value of the tube current to the actual value of the tube current.

In 818, the process 800 may update the iteration number. For example, the process 800 may update the iteration number according to an increment. The increment may be 1 or any other value. For example, the iteration number N may be updated to N+1, and N may be any value. After updating the iteration number, the process 800 may proceed to step 806. If the iteration number does not exceed an iteration-number threshold, the process 800 may repeat operations of steps 806 through 818.

It should be noted that the above description of the generation of the filament current calibration data of the calibration point is provided merely for illustration, and is not intended to limit the scope of the present disclosure. It may be appreciated that for persons having ordinary skills in the art, after understanding the principle of the present invention, changes can be made on the method for generating the filament current calibration data of the calibration point, and various modifications and changes in forms and details of the application of performing the above control flow can be made without departing from the scope of the principle. For example, the order of the steps may be adjusted, or some steps may be added or removed. As another example, a ratio of the actual value of the tube current to the preset value of the tube current may be calculated in step 814. Whether the preset value of the tube current is updated to the actual value of the tube current may be determined based on the ratio.

FIG. 9 illustrates a flowchart of an exemplary process 900 for X-ray tube preheating plan generation according to some embodiments of the present disclosure. One or more operations in the process 900 may be implemented by the imaging control device 120. Specifically, in some embodiments, one or more operations in the process 900 may be implemented by the preheating module 420. In some embodiments, step 520 in FIG. 5 may be implemented by performing one or more operations in the process 900.

In 910, the process 900 may determine a value of tube voltage, a value of tube current and a start time for emission based on an emission plan. The emission plan may be obtained from the I/O module 430, the storage module 440, or the database 150. The emission plan may include the value of the tube voltage, the value of the tube current and the start time for emission.

In 920, the process 900 may determine a start time for preheating. The determination of the start time for preheating may be implemented by the preheating time determination unit 423. The start time for preheating may be the time when the high voltage generator 320 starts to perform a filament preheating operation. The start time for preheating may be the time of obtaining the emission plan. For example, if the time of obtaining the emission plan is 10:00 PM, the start time for preheating may be 10:00 PM. The start time for preheating may be the current time of the system. The start time for preheating may also be a time independent of the current time of the system.

In 930, the process 900 may determine a time length of preheating of a filament based on the start time for emission and the start time for preheating. The determination of the time length of preheating of the filament may be implemented by the preheating time determination unit 423. The time length of preheating of the filament may be a time difference between the start time for preheating and the start time for emission. For example, the start time for preheating may be 09:40 PM and the start time for emission may be 09:45 PM, the time length of preheating may be 5 minutes.

In 940, the process 900 may establish a heating model. The heating model may include a corresponding relationship of a value of the tube voltage, a value of the tube current, a time length of preheating of a filament, and filament preheating current. The filament preheating current may correspond to filament current in a filament preheating process. The heating model may be a data table, a multivariate function, and a graph (e.g., a straight line).

In some embodiments, the heating model may be a look-up table. The look-up table may include a corresponding relationship of the value of the tube current, the time length of preheating of the filament, and the filament preheating current at given tube voltage. The look-up table may include a value of the tube current, a time length of a first standard preheating, a time length of a second standard preheating, first current of the filament preheating, second current of the filament preheating, and third current of the filament preheating. The time length of the second standard preheating may be larger than the time length of the first standard preheating. The time length of the first standard preheating and the time length of the second standard preheating may be default values of the imaging system 100. If the time length of preheating of the filament is smaller than the time length of the first standard preheating, the filament preheating current in the preheating plan may be determined as a value of a first filament preheating current based on the value of the tube current. If the time length of preheating of the filament is larger than or equal to the time length of the first standard preheating and smaller than the time length of the second standard preheating, the filament preheating current in the preheating plan may be determined as a value of a second filament preheating current based on the value of the tube current. If the time length of preheating of the filament is larger than or equal to the time length of the second standard preheating, the filament preheating current in the preheating plan may be determined as a value of a third filament preheating current based on the value of the tube current.

For example, Table 2 shows a look-up table corresponding to tube voltage of 80 kV. Specifically, Table 2 shows the corresponding relationship of the tube current, the time length of preheating of the filament, and the filament preheating current at tube voltage of 80 kV, wherein, t1 is the time length of the first standard preheating, and t2 is the time length of the second standard preheating which is larger than the time length of the first standard preheating. t1 and t2 may be default values set by the imaging system 100. As shown in Table 2, taking tube current of 10 mA as an example, when the time length of preheating of the filament is smaller than t1, the filament preheating current is 3.3732 A (the value of the first filament preheating current); when the time length of preheating of the filament is larger than or equal to t1 and smaller than t2, the filament preheating current is 3.3232 A (the value of the second filament preheating current); and when the time length of preheating of the filament is larger than or equal to t2, the filament preheating current is 3.2589 A (the value of the third filament preheating current). For a definite value of the tube voltage and a definite value of the tube current, the value of the filament preheating current may decrease as the increasing of the preheating time length.

TABLE 2

Preheating Plan Look-up Table at Tube Voltage of 80 Kv.

| | Time Length of Preheating of a filament | | |
| --- | --- | --- | --- |
| Tube Current | <t1 First Filament Preheating Current (A) | t1 Second Filament Preheating Current (A) | t2 Third Filament Preheating Current (A) |
| 10 mA | 3.3732 | 3.3232 | 3.2589 |
| 20 mA | 3.5315 | 3.4815 | 3.432 |
| 30 mA | 3.6444 | 3.5944 | 3.5413 |
| 40 mA | 3.7335 | 3.6835 | 3.6168 |
| 50 mA | 3.8077 | 3.7577 | 3.6916 |
| 60 mA | 3.8715 | 3.8215 | 3.7703 |
| 70 mA | 3.9278 | 3.8778 | 3.8195 |
| 80 mA | 3.9783 | 3.9283 | 3.8742 |
| 90 mA | 4.0241 | 3.9741 | 3.9115 |
| 100 mA | 4.0662 | 4.0162 | 3.9441 |
| 110 mA | 4.1051 | 4.0551 | 4.0018 |
| 120 mA | 4.1413 | 4.0913 | 4.0324 |
| . . . | . . . | . . . | . . . |

In 950, the process 900 may generate a filament preheating plan based on the value of the tube voltage, the value of the tube current, the time length of preheating of the filament, and the heating model. The operation of generating the filament preheating plan may be implemented by the preheating plan generation unit 425. The filament preheating plan may include information such as a value of the filament preheating current, and time information corresponding to the value of the filament preheating current. The time information may include information related to the time such as one or more time points (e.g., a start time, an end time, a specific moment (e.g., 9 PM)), and time periods (e.g., 3 seconds, 1 to 2 seconds). For example, the filament preheating plan may be that the preheating is performed with filament preheating current of 10 mA and the preheating time length is 3 seconds. As another example, the filament preheating plan may be that the preheating is performed with filament preheating currents of 10 mA and 5 mA, specifically the preheating is performed with filament preheating current of 10 mA in the first to second seconds, and the preheating is performed with filament preheating current of 5 mA in the second to third seconds.

In some embodiments, as shown in Table 2, when the time length of preheating of the filament is smaller than t1, the filament preheating current is the value of the first filament preheating current; when the time length of preheating of the filament is larger than or equal to t1 and smaller than t2, the filament preheating current is the value of the second filament preheating current; and when the time length of preheating of the filament is larger than t2, the filament preheating current is the value of the third filament preheating current.

In some embodiments, the time length of preheating of the filament may be same as an actual time length of heating of the filament. In some embodiments, the actual time length of heating of the filament may be set to a fixed value or a variable value based on different time lengths of preheating. For example, as shown in Table 2, when the time length of preheating of the filament is smaller than t1, the filament preheating current is the value of the first filament preheating current, the actual time length of heating of the filament may be the time length of preheating; when the time length of preheating of the filament is larger than or equal to t1 and smaller than t2, the filament preheating current is the value of the second filament preheating current, the actual time length of heating of the filament may be t1; and when the time length of preheating of the filament is larger than t2, the filament preheating current is the value of the third filament preheating current, the actual time length of heating of the filament may be t2.

It should be noted that the above description of the process for generating the X-ray tube preheating plan is provided merely for illustration, and is not intended to limit the scope of the present disclosure. It may be appreciated that for persons having ordinary skills in the art, after understanding the principle of the system, various modifications and changes in forms and details can be made on the specific ways and steps of the process 900 of generating the X-ray tube preheating plan, however, these modifications and changes may not depart from the scope of the claims of the present disclosure. For example, in Table 2, the segment number of the time length of preheating of the filament and the filament preheating current may be 3 as shown in Table 2, and may also be 4, 5, etc.

Figure 10:
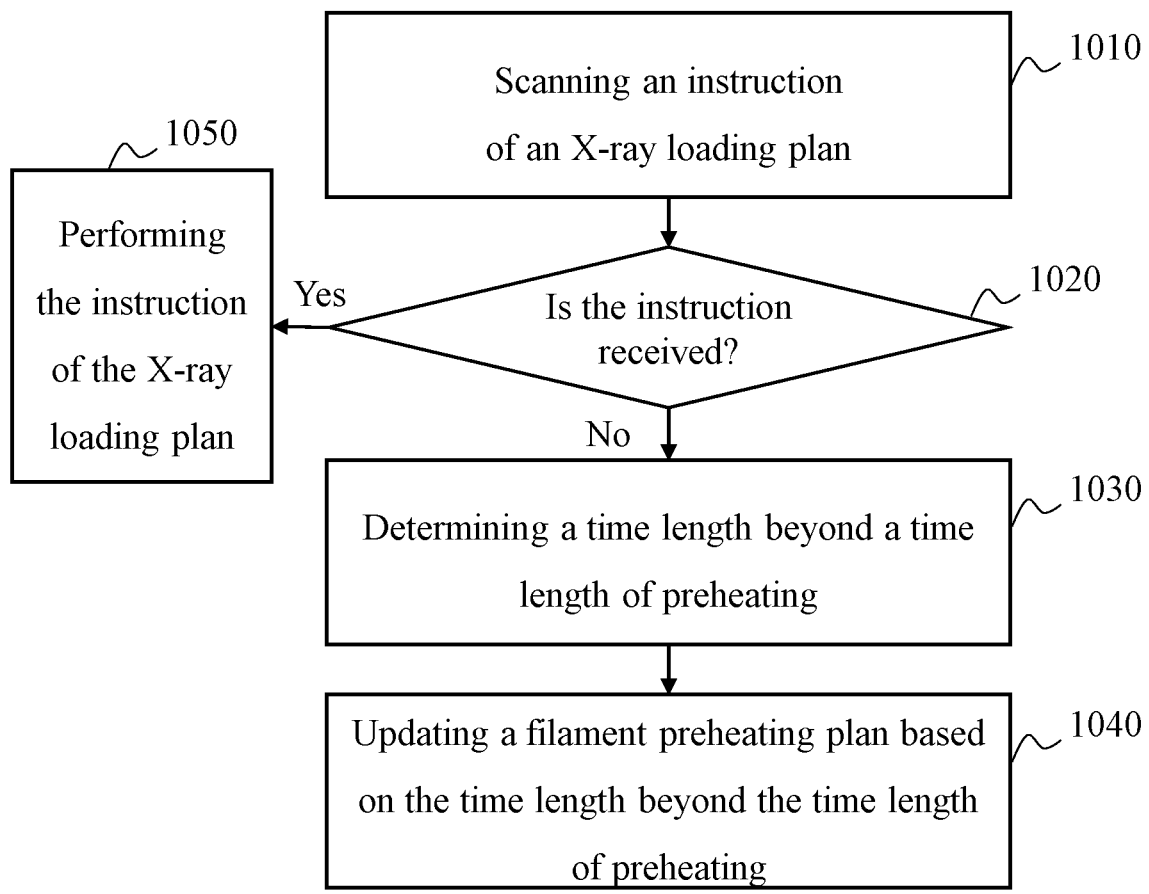
FIG. 10 illustrates a flowchart of an exemplary process for X-ray tube preheating plan generation according to some embodiments of the present disclosure.

FIG. 10 illustrates a flowchart of an exemplary process 1000 for X-ray tube preheating plan generation according to some embodiments of the present disclosure. One or more operations in the process 1000 may be implemented by the imaging control device 120. In some embodiments, step 530 in FIG. 5 may be implemented by performing one or more operations in the process 1000.

In 1010, the process 1000 may scan an instruction of an X-ray loading plan. The operation of scanning the X-ray loading plan may be implemented by the master processor 1212. The imaging system 100 may perform an emission operation based on the instruction of the X-ray loading plan.

In 1020, the process 1000 may determine whether the instruction of the X-ray loading plan is received. The operation of determining whether the instruction of the X-ray loading plan is received may be implemented by the master processor 1212. If the instruction of the X-ray loading plan is received, the process 1000 may proceed to step 1050. If the instruction of the X-ray loading plan is not received, the process may proceed to step 1030.

In 1050, the process 1000 may perform the instruction of the X-ray loading plan. The operation of performing the instruction of the X-ray loading plan may be performing an emission operation according to an emission plan.

In 1030, the process 1000 may determine a time length beyond a time length of preheating. The operation of determining the time length beyond the time length of preheating may be implemented by the preheating module 420.

In 1040, the process 1000 may update a filament preheating plan based on the time length beyond the time length of preheating. The operation of updating the filament preheating plan may be implemented by the preheating module 420. The operation of updating the filament preheating plan may include the determination of information such as one or more filament preheating current, and time information corresponding to the one or more filament preheating current. The filament preheating plan may be updated based on a heating model. The heating model may include a corresponding relationship of a time length of preheating, a time length beyond the time length of preheating, tube current, filament preheating current, etc.

In some embodiments, after the circuit completes the preheating according to an original preheating plan, the master processor may still not receive the instruction of the X-ray loading plan, and the emission is still not started. To ensure that the filament temperature will not exceed a target value due to long-time heating, the filament preheating may be controlled by using a method of changing the values of the filament preheating current in different time segments, and thus obtaining good tube current performance.

In some embodiments, the filament preheating plan may be updated by a functional operation. For example, information of the filament preheating current and corresponding time information in the time length beyond the time length of preheating may be calculated according to the time length of preheating and the time length beyond the time length of preheating.

In the heating model, the time length beyond the time length of preheating may include a first timeout length (e.g., $\Delta t1$) and a second timeout length (e.g., $\Delta t2$). The heating model may include first timeout filament preheating current corresponding to the first timeout length and second timeout filament preheating current corresponding to the second timeout length. If the preheating time ends and the instruction of the X-ray loading plan is not received, the preheating may be performed in the range of the first timeout length with the first timeout filament preheating current. If the second timeout length ends and the instruction of the X-ray loading plan is not received, the preheating may be performed in the range of the second timeout length with the second timeout filament preheating current. Similarly, if the N-th timeout length ends and the instruction of the X-ray loading plan is not received, the preheating may be performed in the range of the N-th timeout length with the N-th timeout filament preheating current. In some embodiments, after the second timeout length ends, if the instruction of the X-ray loading plan is not received, the filament preheating current may be maintained as the second timeout filament preheating current.

In some embodiments, the filament preheating plan may be updated via the look-up Table 3. For example, Table 3 shows the corresponding relationship of the tube current, the time length of preheating, the time length beyond the time length of preheating, and the filament preheating current at tube voltage of 80 kV. Wherein, t1 is a time length of preheating, the value of the filament preheating current corresponding to the time length of preheating is a value of a fourth current of the filament preheating. After the time length of preheating t1 ends, if the instruction of the X-ray loading plan is not received, a time length $\Delta t1$ beyond the time length of preheating and a value of first timeout filament preheating current corresponding to the time length $\Delta t1$ beyond the time length of preheating may be determined. After the time lengths of t1 and $\Delta t1$ end, if the instruction of the X-ray loading plan is not received, a time length $\Delta t2$ beyond the time length of preheating and a value of second timeout filament preheating current corresponding to the time length $\Delta t2$ beyond the time length of preheating may be determined. For convenience, the filament preheating current after $\Delta t2$ may be maintained as the value of the second timeout filament preheating current. In Table 3, n in $\Delta tn$ is an integer greater than 2.

TABLE 3

Preheating Plan Updating Look-up Table at Tube Voltage of 80 kV.

| | Tube Voltage 80 kV | | |
|---|---|---|---|
| | Time Length of Preheating | Time Length beyond the Time Length of Preheating | |
| Tube Current | t1 Value of the Fourth Filament Preheating Current (A) | $\Delta t1$ Value of the First Timeout Filament Preheating Current (A) | $\Delta t2 \sim \Delta tn$ Value of the Second Timeout Filament Preheating Current (A) |
| 10 mA | 3.3232 | 3.2732 | 3.2446 |
| 20 mA | 3.4815 | 3.4365 | 3.4275 |
| 30 mA | 3.5944 | 3.5494 | 3.5332 |
| 40 mA | 3.6835 | 3.6335 | 3.6001 |
| 50 mA | 3.7577 | 3.7027 | 3.6805 |
| 60 mA | 3.8215 | 3.7715 | 3.7691 |
| 70 mA | 3.8778 | 3.8228 | 3.8162 |
| 80 mA | 3.9283 | 3.8783 | 3.8701 |
| 90 mA | 3.9741 | 3.9191 | 3.9039 |
| 100 mA | 4.0162 | 3.9562 | 3.932 |
| 110 mA | 4.0551 | 4.0061 | 3.9975 |
| 120 mA | 4.0913 | 4.0368 | 4.028 |
| ... | ... | ... | ... |

It should be noted that the above description of the process for generating the X-ray tube preheating plan is provided merely for illustration, and is not intended to limit the scope of the present disclosure. It may be appreciated that for persons having ordinary skills in the art, after understanding the principle of the system, various modifications and changes in forms and details can be made on the specific ways and steps of the process 1000, however, these modifications and changes may not depart from the scope of the claims of the present disclosure. For example, in Table 3, the filament preheating current after $\Delta t2$ may be variable.

FIG. 11 illustrates a flowchart of an exemplary process 1100 for filament preheating plan generation according to some embodiments of the present disclosure. One or more operations in the process 1100 may be implemented by the imaging control device 120. In some embodiments, step 550 in FIG. 5 may be implemented by performing one or more operations in the process 1100.

In 1110, the process 1100 may determine a value of tube voltage, a value of tube current and a start time for emission based on an emission plan. The operation of determining the value of the tube voltage, the value of the tube current and the start time for emission may be implemented by the preheating module 420. The emission plan may be obtained from the I/O module 430, the storage module 440, or the database 150. The emission plan may include the value of the tube voltage, the value of the tube current and the start time for emission.

In 1120, the process 1100 may determine a start time for preheating. The operation of determining the start time for preheating may be implemented by the preheating module 420. The start time for preheating may be the time of starting to perform a filament preheating operation by the high voltage generator 320.

In 1130, the process 1100 may determine a time length of preheating of a filament based on the start time for emission and the start time for preheating. The operation of determining the time length of preheating of the filament may be implemented by the preheating module 420. The time length of preheating of the filament may be a time interval between the start time for preheating and the start time for emission. For example, if the start time for preheating is 09:40 PM and the start time for emission is 09:45 PM, the time length of preheating of the filament may be 5 minutes.

In 1140, the process 1100 may establish a heating model. The operation of determining the heating model may be implemented by the preheating module 420. The heating model may include the corresponding relationship of tube voltage, tube current, a time length of preheating of a filament, a filament temperature, filament preheating current, etc. The filament preheating current may correspond to filament current during a filament preheating stage. The heating model may be presented in forms of a data table or a function. According to the data table, the process 1100 may determine filament preheating current corresponding to the tube voltage, the tube current, the time length of preheating of the filament, and the filament temperature. According to the function, the process 1100 may determine filament preheating current corresponding to the tube voltage, the tube current, the time length of preheating of the filament, and the filament temperature.

In 1150, the process 1100 may determine a filament temperature. The operation of determining the filament temperature may be implemented by the preheating module 420. The filament temperature may be an initial value of the filament temperature when the process 1100 initiates. The initial value of the filament temperature may be a result of the previous emission. The filament temperature may be obtained from a component or a device (e.g., a thermometer) in the imaging system. The filament temperature may also be determined by the calculation of the imaging system 100. In some embodiments, the process 1100 may determine an equivalent description value of the filament temperature. The equivalent description value may describe the thermionic emission capability of the filament. The equivalent description value of the filament temperature may be a result of the previous emission.

According to the previous emission, the process 1100 may determine the initial value of the filament temperature or the equivalent description value of the filament temperature. According to the previous emission, tube voltage of the previous emission, a value of the tube current of the previous emission, and an end time for the previous emission may be determined. A time interval may be determined based on the end time for the previous emission and the start time for emission. The time interval may be a time difference between the end time for the previous emission and the start time for emission. The initial value of the filament temperature or the equivalent description value of the filament temperature may be determined according to the tube voltage of the previous emission, the value of the tube current of the previous emission, and the time interval.

In some embodiments, the process 1100 may determine the initial value of the filament temperature or the equivalent description value of the filament temperature based on a filament temperature model. The filament temperature model may represent the corresponding relationship of a time interval between two times of emission, tube current, and a filament temperature. The filament temperature model may exist in the form of a filament radiation table. The filament radiation table may include the corresponding relationship of the tube voltage of the previous emission, the tube current of the previous emission, the time interval between two times of emission, one or more time ranges, and one or more filament temperatures. The one or more time ranges may include a first time range (e.g., 0 to t1), a second time range (e.g., t1 to t2), a third time range (e.g., t2 to t3), and a fourth time range (e.g., greater than t3). In the radiation table, a filament temperature corresponding to different values of the tube current and time ranges may be stored. The first time range, the second time range, the third time range, and the fourth time range may be time ranges segmented by a first time point (e.g., a time point t1), a second time point (e.g., a time point t2), and a third time point (e.g., a time point t3). The first time point, the second time point, and the third time point may be obtained by calculation of the imaging system or determined by a user (e.g., a value determined by a user based on experience). The filament temperature may be determined by looking up the filament radiation table according to the time interval between the two times of emission, and the tube current of the previous emission.

For example, a filament radiation table corresponding to different time intervals and tube currents as shown in Table 4 may be obtained from the heating model 1213. Table 4 shows the corresponding relationship of the tube current, the time interval, and the filament temperature at tube voltage of 80 kV. As shown in Table 4, for a definite value of the tube voltage and a definite value of the tube current, when the time interval falls into different time ranges (e.g., 0 to t1 (corresponding to tc1 in Table 4), t1 to t2 (corresponding to tc2 in Table 5), t2 to t3 (corresponding to tc3 in Table 5)), corresponding filament temperature may be obtained (e.g., T3° C., T2° C., T1° C., 0° C.). For example, when the value of the tube current is 50 mA, if the time interval falls within the time range of t1 to t2, the corresponding filament temperature is 0° C. As another example, when the value of the tube current is 200 mA, if the time interval falls within the time range of t1 to t2, the corresponding filament temperature is T1° C.

TABLE 4

Filament Radiation Table of different Time Intervals and Tube Current.

| | Tube Voltage 80 kV Time Interval | | | |
|---|---|---|---|---|
| Tube Current | 0~t1 Filament Temperature (° C.) | t1~t2 Filament Temperature (° C.) | t2~t3 Filament Temperature (° C.) | >t3 Filament Temperature (° C.) |
| 50 mA | T1 | 0 | 0 | 0 |
| 100 mA | T2 | 0 | 0 | 0 |
| 150 mA | T2 | 0 | 0 | 0 |
| 200 mA | T2 | T1 | 0 | 0 |
| 250 mA | T2 | T1 | 0 | 0 |
| 300 mA | T3 | T1 | T1 | 0 |
| 350 mA | T3 | T1 | T1 | 0 |
| 400 mA | T3 | T2 | T1 | 0 |
| 450 mA | T3 | T2 | T1 | 0 |
| 500 mA | T3 | T2 | T2 | 0 |
| 550 mA | T3 | T2 | T2 | 0 |
| 600 mA | T3 | T2 | T2 | 0 |
| ... | T3 | T2 | T2 | 0 |

In 1160, the process 1100 may generate a filament preheating plan based on the value of the tube voltage, the value of the tube current, the time length of preheating of the filament, the filament temperature, and the heating model.

The operation of generating the filament preheating plan may be implemented by the preheating module 420. The filament preheating plan may include information such as filament preheating current, and time information corresponding to the filament preheating current.

In some embodiments, the heating model may exist in the form of a data table. The data table may include tube voltage, a first standard preheating time, a second standard preheating time, a value of the tube current, a value of the filament preheating current, a filament temperature, etc. The second standard preheating time may be larger than the first standard preheating time. The filament temperature may include a first filament temperature, a second filament temperature, and a third filament temperature. The first filament temperature, the second filament temperature, and the third filament temperature may be determined based on a filament temperature model. The process 1100 may determine filament preheating current based on the filament temperature, the value of the tube voltage, the value of the tube current, the relationship of the time length of preheating of the filament, the first standard preheating time and the second standard preheating time, and the heating model.

For example, the heating model may exist in the form of a look-up table. The look-up table may include the corresponding relationship of a time length of preheating of a filament, tube voltage, a filament temperature, and tube current. The time length of preheating of the filament may include a time length of a first standard preheating and a time length of a second standard preheating. The time length of the second standard preheating may be larger than the time length of the first standard preheating. The filament temperature may include a first filament temperature, a second filament temperature, and a third filament temperature. In some embodiments, the filament temperature may be determined in step 1150. The first filament temperature may correspond to a first range (e.g., tc1 (corresponding to the range of 0 to t1 in table 4)), the second filament temperature may correspond to a second range (e.g., tc2 (corresponding to the range of t1 to t2 in table 4)), and the third filament temperature may correspond to a third range (e.g., tc3 (corresponding to the range of t2 to t3 in table 4)). A filament preheating temperature may be determined via the look-up table based on the filament temperature, the value of the tube current, the value of the tube voltage and the time length of preheating of the filament.

For example, Table 5 shows the corresponding relationship of tube current, a time length of preheating of a filament, a filament temperature, and filament preheating current at tube voltage of 80 kV. Wherein, a t1 is a time length of a first standard preheating, a t2 is a time length of a second standard preheating larger than the time length of the first standard preheating, and t1 and t2 may be default values set by the imaging system 100. A tc1 is a first time range. A tc2 is a second time range. A tc3 is a third time range. A T1 is a first filament temperature corresponding to the first time range. A T2 is a second filament temperature corresponding to the second time range. A T3 is a third filament temperature corresponding to the third time range. For a definite value of the tube voltage, a definite value of the tube current, a definite time length of preheating of the filament, and a definite filament temperature, the corresponding filament preheating current may be determined via the look-up table 5. Taking tube current of 10 mA as an example, when the time length of preheating of the filament is smaller than t1 and the filament temperature is T1° C., the filament preheating current corresponding to the time length of preheating may be determined to 3.17664 A via Table 5.

TABLE 5

Look-Up Table of the Time Length of Preheating of a filament and corresponding Value of the Tube Current.

| Tube current (mA) | Tube voltage 80 kV Time length of preheating of a filament | | | | | | | | |
|---|---|---|---|---|---|---|---|---|---|
| | <t1 | | | t1 | | | t2 | | |
| | tc1 T1 | tc2 T2 | tc3 T3 | tc1 T1 | tc2 T2 | tc3 T3 | tc1 T1 | tc2 T2 | tc3 T3 |
| | Filament preheating current (A) | | | | | | | | |
| 10 mA | 3.17664 | 3.2232 | 3.3732 | 3.1672 | 3.2032 | 3.3232 | 3.11538 | 3.11226 | 3.2589 |
| 20 mA | 3.33494 | 3.3815 | 3.5315 | 3.3255 | 3.3615 | 3.4815 | 3.28848 | 3.28536 | 3.432 |
| 30 mA | 3.46422 | 3.5069 | 3.6444 | 3.4514 | 3.4844 | 3.5944 | 3.40974 | 3.40688 | 3.5413 |
| 40 mA | 3.55332 | 3.596 | 3.7335 | 3.5405 | 3.5735 | 3.6835 | 3.48524 | 3.48238 | 3.6168 |
| 50 mA | 3.62752 | 3.6702 | 3.8077 | 3.6147 | 3.6477 | 3.7577 | 3.56004 | 3.55718 | 3.6916 |
| 60 mA | 3.6636 | 3.734 | 3.8715 | 3.6565 | 3.7115 | 3.8215 | 3.6185 | 3.6152 | 3.7703 |
| 70 mA | 3.7199 | 3.7903 | 3.9278 | 3.7128 | 3.7678 | 3.8778 | 3.6677 | 3.6644 | 3.8195 |
| 80 mA | 3.7704 | 3.8408 | 3.9783 | 3.7633 | 3.8183 | 3.9283 | 3.7224 | 3.7191 | 3.8742 |
| 90 mA | 3.80675 | 3.88035 | 4.0241 | 3.8016 | 3.8591 | 3.9741 | 3.7528 | 3.74935 | 3.9115 |
| 100 mA | 3.84885 | 3.92245 | 4.0662 | 3.8437 | 3.9012 | 4.0162 | 3.7854 | 3.78195 | 3.9441 |
| 110 mA | 3.88775 | 3.96135 | 4.1051 | 3.8826 | 3.9401 | 4.0551 | 3.8431 | 3.83965 | 4.0018 |
| 120 mA | 3.92395 | 3.99755 | 4.1413 | 3.9188 | 3.9763 | 4.0913 | 3.8737 | 3.87025 | 4.0324 |
| . . . | . . . | . . . | . . . | . . . | . . . | . . . | . . . | . . . | . . . |

It should be noted that the above description of the process for generating the filament preheating plan is provided merely for illustration, and is not intended to limit the scope of the present disclosure. It may be appreciated that for persons having ordinary skills in the art, after understanding the principle of the system, various modifications and changes in forms and details can be made on the specific ways and steps of the process 1100, however, these modifications and changes may not depart from the scope of the claims of the present disclosure. For example, the process 1100 may first operate for determining the filament temperature in step 1150, and then operate for determining the heating model in step 1140.

Figure 12:
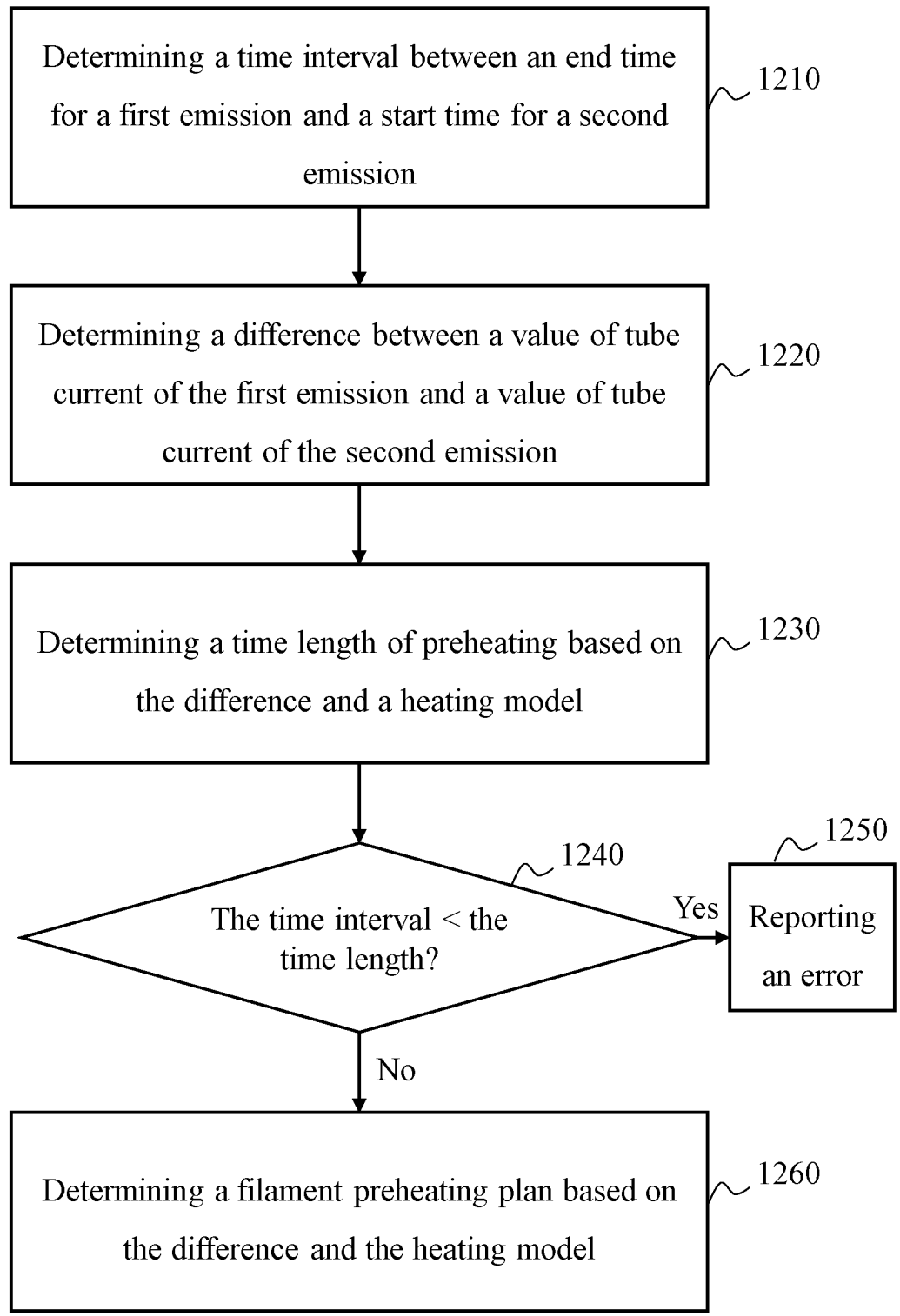
FIG. 12 illustrates a flowchart of an exemplary process for filament preheating plan generation according to some embodiments of the present disclosure.

FIG. 12 illustrates a flowchart of an exemplary process 1200 for filament preheating plan generation according to some embodiments of the present disclosure. One or more operations in the process 1200 may be implemented by the imaging control device 120. In some embodiments, step 550 in FIG. 5 may be implemented by performing one or more operations in the process 1200.

In 1210, the process 1200 may determine a time interval between an end time for a first emission and a start time for a second emission. The operation of determining the time interval may be implemented by the preheating module 420. The end time for the first emission and the start time for the second emission may be determined based on a first emission plan and a second emission plan. The first emission plan may include a value of tube current of the first emission, a value of tube voltage of the first emission, a start time for the first emission, the end time for the first emission, etc. The second emission plan may include a value of the tube current of the second emission, a value of the tube voltage of the second emission, the start time for the second emission, an end time for the second emission, etc. The time interval may be a time difference between the start time for the second emission and the end time for the first emission. For example, if the start time for the second emission is 10:30 PM, the end time for the first emission is 10:00 PM, and the time interval is 30 minutes.

In 1220, the process 1200 may determine a difference between a value of the tube current of the first emission and a value of the tube current of the second emission. The operation of determining the difference may be implemented by the preheating module 420. In some embodiments, the difference may be a current difference obtained by subtracting the value of the tube current of the second emission from the value of the tube current of the first emission. The value of the tube current of the second emission may be larger than, smaller than or equal to the value of the tube current of the first emission.

In 1230, the process 1200 may determine a time length of preheating based on the difference and a heating model. The operation of determining the time length of preheating may be implemented by the preheating module 420. The heating model may include the corresponding relationship of the difference, the tube voltage of the second emission, the time interval, filament preheating current, the time length of preheating, etc. The time length of preheating may be a time length through which the value of the tube current of the first emission is increased, decreased, or maintained at the value of the tube current of the second emission. The time length of preheating may be a time length through which the filament temperature is changed to a second filament temperature.

In some embodiments, the heating model may be a look-up table in the heating model 1213. For example, the value of the tube current of the first emission is 10 mA, the value of the tube current of the second emission is 20 mA, the difference is 10 mA. According to the look-up table, a time length of preheating corresponding to the difference of 10 mA may be determined.

In some embodiments, the heating model may be a function. The time length of preheating may be determined by way of functional operation based on the function, the difference, the time interval, etc. The filament preheating current may be filament current corresponding to a value of the tube current which is increased, decreased, or maintained at the value of the tube current of the first emission to the value of the tube current of the second emission. In some embodiments, the filament current of which the value of the tube current of the first emission is changed to the value of the tube current of the second emission may be called a sustaining current.

In 1240, the process 1200 may determine whether the time interval is smaller than the time length of preheating. If the time interval is smaller than the time length of preheating, the process 1200 may proceed to step 1250. If the time interval is not smaller than the time length of preheating, the process 1200 may proceed to step 1260.

In 1250, the process 1200 may report an error. The operation of reporting the error may be implemented by the preheating module 420. The error may include information such as the time interval, the time length of preheating, etc. The error may be sent to the terminal 130 or displayed on the display 140. For example, the value of the tube current of the first emission is 10 mA, the value of the tube current of the second emission is 20 mA, the time interval is smaller than 1 second, but the corresponding time length of preheating of increasing the value of the tube current from 10 mA to 20 mA is larger than 1 second. In the condition of a time interval smaller than 1 second, the value of the tube current of the second emission cannot be increased from 10 mA to 20 mA, and thus reporting an error. As another example, the value of the tube current of the first emission is 20 mA, the value of the tube current of the second emission is 10 mA, the time interval is smaller than 1 second, but the corresponding time length of preheating of decreasing the value of the tube current from 20 mA to 10 mA is larger than 1 second. In the condition of a time interval smaller than 1 second, the value of the tube current of the second emission cannot be decreased from 20 mA to 10 mA, and thus reporting an error.

In 1260, the process 1200 may determine a filament preheating plan based on the difference and the heating model. The filament preheating plan may include information such as filament preheating current, and time information corresponding to the filament preheating current, etc.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "block," "module," "module," "unit," "component," or "system." Furthermore, aspects of the present disclosure may take the form of a computer program product embodied in one or more computer readable media having computer readable program code embodied thereon.

A computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for preheating a filament of an X-ray tube, comprising:
    determining a value of tube voltage, a value of tube current, a start time for emission, and a start time for preheating;
    determining, based on the start time for emission and the start time for preheating, a time length of preheating of the filament;
    establishing a heating model, wherein the heating model includes a corresponding relationship of the value of the tube current, the time length of preheating of the filament, and a filament preheating current at a given tube voltage, and the heating model includes a time length of a first standard preheating and a time length of a second standard preheating;
    determining a filament preheating plan according to the value of the tube voltage, the value of the tube current, the time length of preheating of the filament, and the heating model, wherein the determining the filament preheating plan according to the value of the tube voltage, the value of the tube current, the time length of preheating of the filament, and the heating model includes:
  determining a filament preheating current of the filament preheating plan by comparing the time length of the preheating of the filament with the time length of the first standard preheating and the time length of the second standard preheating; and
performing, based on the filament preheating plan, a filament-preheating operation.

2. The method of claim 1, wherein the filament preheating plan further includes one or more time points or time periods corresponding to the filament preheating current.

3. The method of claim 1, wherein the determining the filament preheating current of the filament preheating plan by comparing the time length of the preheating of the filament with the time length of the first standard preheating and the time length of the second standard preheating includes:
  if the time length of preheating of the filament is smaller than the time length of the first standard preheating, determining the filament preheating current as a first filament preheating current;
  if the time length of preheating of the filament is larger than or equal to the time length of the first standard preheating and smaller than the time length of the second standard preheating, determining the filament preheating current as a second filament preheating current; and
  if the time length of preheating of the filament is larger than or equal to the if the time length of preheating of the filament is larger than or equal to the second standard preheating time length, determining the filament preheating current as a third filament preheating current.

4. The method of claim 1, wherein performing, based on the filament preheating plan, the filament-preheating operation comprises:
  determining whether an instruction of an X-ray loading plan is received; and
  performing, based on the determination as to whether an instruction of an X-ray loading plan is received, at least one operation.

5. The method of claim 4, wherein performing, based on the determination as to whether an instruction of an X-ray loading plan is received, the at least one operation comprises:
  determining, based on a determination of not receiving the instruction of an X-ray loading plan, a time length beyond the time length of preheating of the filament; and
  updating, based on the time length beyond the time length of preheating of the filament, the filament preheating plan.

6. The method of claim 4, wherein performing, based on the determination as to whether an instruction of an X-ray loading plan is received, the at least one operation comprises:
  performing, based on a determination of receiving the instruction of an X-ray loading plan, the instruction of the X-ray loading plan.

7. The method of claim 1, wherein determining the filament preheating plan further comprises:
  determining an initial value or an equivalent description value of a filament temperature; and
  determining, based on the initial value or the equivalent description value of the filament temperature, the filament preheating plan.

8. The method of claim 7, wherein determining the initial value or the equivalent description value of the filament temperature further comprises:
  obtaining a first emission plan and a second emission plan; and
  determining, based on the first emission plan and the second emission plan, the initial value or the equivalent description value of the filament temperature.

9. The method of claim 8, wherein determining, based on the initial value or the equivalent description value of the filament temperature, the filament preheating plan further comprises:
  determining an emission time interval between an end time for emission of the first emission plan and a start time for emission of the second emission plan;
  determining a difference between a value of the tube current of the first emission plan and a value of the tube current of the second emission plan;
  determining a time length of preheating of a second emission based on the difference and the heating model;
  comparing the emission time interval with the time length of preheating of the second emission; and
  reporting an error when the emission time interval is smaller than the time length of preheating of the second emission.

10. A system for preheating a filament of an X-ray tube, comprising:
  a storage device storing a set of instructions; and
  one or more processors configured to communicate with the storage device, wherein when executing the set of instructions, the one or more processors are configured to cause the system to:
    determine a value of tube voltage, a value of tube current, a start time for emission, and a start time for preheating;
    determine, based on the start time for emission and the start time for preheating, a time length of preheating of the filament;
    establish a heating model, wherein the heating model includes a corresponding relationship of the value of the tube current, the time length of preheating of the filament, and a filament preheating current at a given tube voltage, and the heating model includes a time length of a first standard preheating and a time length of a second standard preheating;
    determine a filament preheating plan according to the value of the tube voltage, the value of the tube current, the time length of preheating of the filament and the heating model, wherein to determine the filament preheating plan according to the value of the tube voltage, the value of the tube current, the time length of preheating of the filament, and the heating model, the one or more processors are further configured to cause the system to:
      determining a filament preheating current of the filament preheating plan by comparing the time length of the preheating of the filament with the time length of the first standard preheating and the time length of the second standard preheating; and
    perform, based on the filament preheating plan, a filament-preheating operation.

11. The system of claim 10, wherein the filament preheating plan further includes one or more time points or time periods corresponding to the filament preheating current.

12. The system of claim 10, wherein
to determine the filament preheating current of the filament preheating plan by comparing the time length of the preheating of the filament with the time length of the first standard preheating and the time length of the second standard preheating, the one or more processors are further configured to cause the system to:
if the time length of preheating of the filament is smaller than the time length of the first standard preheating, determine the value of the filament preheating current as a first filament preheating current;
if the time length of preheating of the filament is larger than or equal to the time length of the first standard preheating and smaller than the time length of the second standard preheating, determine the value of the filament preheating current as a second filament preheating current; and
if the time length of preheating of the filament is larger than or equal to the time length of the second standard preheating, determine the value of the filament preheating current as a third filament preheating current.

13. The system of claim 10, wherein to perform, based on the filament preheating plan, a filament-preheating operation, the one or more processors are further configured to cause the system to:
determine whether an instruction of an X-ray loading plan is received, and
perform, based on the determination as to whether an instruction of an X-ray loading plan is received, at least one operation.

14. The system of claim 13, wherein to perform, based on the determination as to whether an instruction of an X-ray loading plan is received, at least one operation, the one or more processors are further configured to cause the system to:
determine, based on a determination of not receiving the instruction of an X-ray loading plan, a time length beyond the time length of preheating of the filament; and
update, based on the time length beyond the time length of preheating of the filament, the filament preheating plan to perform at least one operation based on the determination as to whether an instruction of an X-ray loading plan is received.

15. The system of 13, wherein to perform, based on the determination as to whether an instruction of an X-ray loading plan is received, at least one operation, the one or more processors are further configured to cause the system to:
perform, based on a determination of receiving the instruction of an X-ray loading plan, the instruction of the X-ray loading plan to perform at least one operation based on the determination as to whether an instruction of an X-ray loading plan is received.

16. The system of claim 10, wherein to determine the filament preheating plan, the one or more processors are further configured to cause the system to:
determine an initial value or an equivalent description value of a filament temperature; and
determine, based on the initial value or the equivalent description value of the filament temperature, the filament preheating plan.

17. The system of claim 16, wherein to determine the initial value or the equivalent description value of the filament temperature, the one or more processors are further configured to cause the system to:
obtain a first emission plan and a second emission plan; and
determine, based on the first emission plan and the second emission plan, the initial value or the equivalent description value of the filament temperature.

18. The system of claim 17, wherein to determine, based on the first emission plan and the second emission plan, the initial value or the equivalent description value of the filament temperature, the one or more processors are further configured to cause the system to:
determine an emission time interval between an end time for emission end time of the first emission plan and a start time for emission of the second emission plan;
determine a difference between a value of the tube current of the first emission plan and a value of the tube current of the second emission plan;
determine a time length of preheating of a second emission based on the difference and the heating model;
compare the emission time interval with the time length of preheating of the second emission; and
report an error when the emission time interval is smaller than the time length of preheating of the second emission.

19. A non-transitory computer readable medium including executable instructions that, when executed by at least one processor, cause the at least one processor to effectuate a method comprising:
determining a value of tube voltage, a value of tube current, a start time for emission, and a start time for preheating;
determining, based on the start time for emission and the start time for preheating, a time length of preheating of a filament;
establishing a heating model, wherein the heating model includes a corresponding relationship of the value of the tube current, the time length of preheating of the filament, and a filament preheating current at a given tube voltage, and the heating model includes a time length of a first standard preheating and a time length of a second standard preheating;
determining a filament preheating plan according to the value of the tube voltage, the value of the tube current, the time length of preheating of the filament and the heating model, wherein the determining the filament preheating plan according to the value of the tube voltage, the value of the tube current, the time length of preheating of the filament, and the heating model includes:
determining a filament preheating current of the filament preheating plan by comparing the time length of the preheating of the filament with the time length of the first standard preheating and the time length of the second standard preheating; and
performing, based on the filament preheating plan, a filament-preheating operation.

* * * * *